United States Patent [19]

Ono et al.

[11] Patent Number: 5,342,940

[45] Date of Patent: Aug. 30, 1994

[54] POLYETHYLENE GLYCOL DERIVATIVES, PROCESS FOR PREPARING THE SAME

[75] Inventors: Keiichi Ono, Sakai; Yoshiyuki Kai, Kobe; Hiroo Maeda, Takatsuki, all of Japan

[73] Assignees: Sumitomo Pharmaceuticals Company, Limited, Osaka; Seikagaku Corporation, Tokyo, both of Japan

[21] Appl. No.: 119,821

[22] Filed: Sep. 13, 1993

Related U.S. Application Data

[60] Division of Ser. No. 950,774, Sep. 24, 1992, which is a continuation of Ser. No. 525,671, May 21, 1990, abandoned.

[30] Foreign Application Priority Data

May 27, 1989 [JP] Japan ................................. 1-134191
May 27, 1989 [JP] Japan ................................. 1-134192

[51] Int. Cl.$^5$ ............................................. C07D 251/26
[52] U.S. Cl. ..................................... 544/218; 435/134
[58] Field of Search ......................... 544/218; 435/134

[56] References Cited

U.S. PATENT DOCUMENTS

4,179,337 12/1979 Davis et al.

FOREIGN PATENT DOCUMENTS

| 149520 | 1/1985 | European Pat. Off. |
| 0210761 | 2/1987 | European Pat. Off. |
| 56-23587 | 6/1981 | Japan |
| 61-178926 | 8/1986 | Japan |
| 61-42558 | 9/1986 | Japan |
| 62-115280 | 5/1987 | Japan |
| 0115280 | 5/1987 | Japan |
| 62-175175 | 7/1987 | Japan |
| 63-10800 | 1/1988 | Japan |
| 1316400 | 12/1989 | Japan |

OTHER PUBLICATIONS

Inada, Chemical Abstract 108(7), 1987, #52017d.

Nishimura et al Chemical Abstract 102(7), 1985 #17245f.

Chemistry Letters, 1980, pp. 773-776, Matsushima et al, "Modification of *E. coli* Asparaginase with 2,4-bis-(o-methoxypolyethylene glycol) . . . ".

Tetrahedron, 40, 1984, pp. 1581-1584, Leonard et al, "Synthesis of Monomethoxypolyoxyethylene-Bound Haemoglobins".

J. Biol. Chem., 252, (1977), 3578-3581, Abuchowski et al, "Alteration of Immunological Properties of Bovine Serum Albumin by Covalent . . . ".

Anal. Biochem., 131, (1983), pp. 25-33, Beauchamp et al, "A New Procedure for the Synthesis of Polyethylene Glycol-Protein Adducts; . . . ".

Seikagaku, 56, (1984), 1481.

Cancer Biochem. Biophys., 7, (1984), pp. 175-186, Abuchowski et al, "Cancer Therapy with Chemically Modified Enzymes. I. Antitumor . . . ".

Chemical Abstracts, vol. 102, No. 7099, 7 Jan. 1985, p. 29.

Patent Abstracts of Japan, vol. 011, No. 332 (C-455) (2779) 27 Oct. 1987, Koichi et al.

Journal of Polymer Science, vol. 24, No. 2, 1986, pp. 375-378; "Preparation of cyanuric-chloride activated poly(ethylene glycol)".

English language translation of *Japanese Journal of Cancer Research*, vol. 77, No. 12, Oct. 1986, pp. 1264-1270; T. Yoshimoto et al., "Characterization of polyethylene glycol modified L-asparaginase from *Escherichia coli* and its application to therapy leukemia".

*Primary Examiner*—Mukund Shah
*Assistant Examiner*—Y. N. Gupta
*Attorney, Agent, or Firm*—Stevens, Davis, Miller & Mosher

[57] ABSTRACT

High purity polyethylene glycol derivatives of formula (I) are useful as protein modifiers of interferons, t-PA, EGF, various hormones, etc. The thus modified protein has minimized antigenicity, prolonged plasma half life, or improved transfer to tissue. A novel process for preparing high purity polyethylene glycol derivatives is also disclosed.

2 Claims, 5 Drawing Sheets

F I G. 6
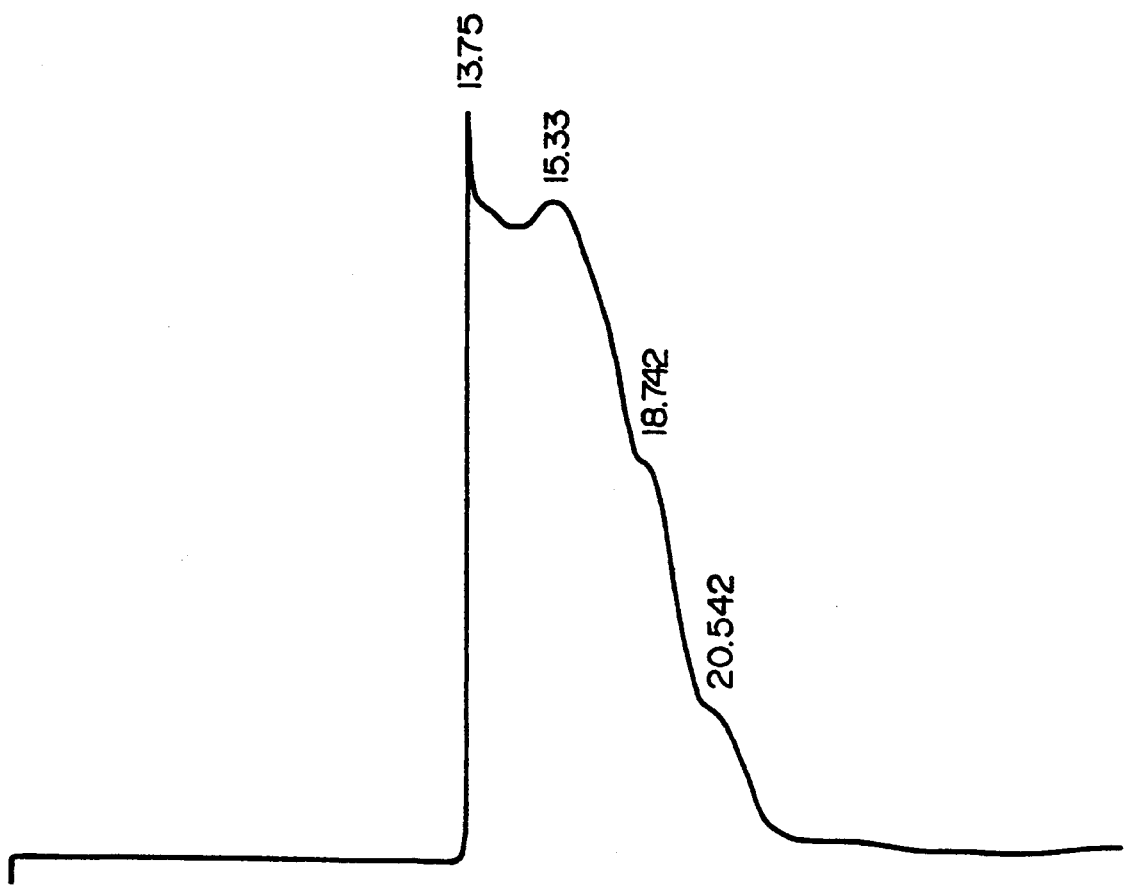

1: HDMA
2: HDMA+PEG2-HDMA
3: PEG2-HDMA

POLYETHYLENE GLYCOL DERIVATIVES, PROCESS FOR PREPARING THE SAME

This application is a divisional of application Ser. No. 07/950,774, filed Sep. 24, 1992; which in turn is a continuation of application Ser. No. 07/525,671, filed May 21, 1990, now abandoned.

BACKGROUND OF THE INVENTION

1. Field of the Invention

The present invention relates to high purity polyethylene glycol derivatives useful as protein modifiers, etc., and a novel process for preparing polyethylene glycol derivatives as well as protein modified by high purity polyethylene glycol derivatives.

2. Related Art Statement

In recent years, it has become possible to produce protein having physiological activities in large quantities due to the progress of genetic engineering technology. Such protein has been expected to be used as a drug. However, when physiologically active protein is provided for practical use as a therapeutic agent, the protein is sometimes ineffective as a therapeutic agent, because its clearance from blood circulation is extremely rapid due to decomposition of the protein by peptidase present in the body, transfer of the protein to the target tissue is not efficient, etc.. Furthermore, there is a danger that immune reaction might be caused when physiologically active protein obtained from the heterologous organism is administered to human. In order to solve these problems, it has been attempted to chemically modify the physiologically active protein with an artificial high molecular compound, especially using polyethylene glycol. In polyethylene glycol, its immunogenicity per se is extremely low; by chemically binding polyethylene glycol to protein, the effects of decreasing antigenicity, decreasing immunogenicity, minimizing toxicity, prolonging plasma half life, etc. are exhibited.

In addition, the polyethylene glycol-bound protein is soluble in an organic solvent so that synthesis using hydrolase (i.e., protein) can be effectively conducted.

For chemically binding polyethylene glycol to protein, the following methods are known: (1) method for introducing two polyethylene glycol mono-alkyl ether chains into amino groups of protein via cyanuric chloride [Inada et al., Japanese Patent Application KOKOKU No. 61-42558; Inada et al., Chemistry Letters, 773 (1980); Inada et al., Japanese Journal of Cancer Research, 77, 1264 (1986); Miyata et al., Japanese Patent Application KOKAI No. 62-115280]; (2) method for introducing polyethylene glycol into amino groups of protein using polyethylene glycol mono-alkyl ether acyl azides (Theodous Fan, N., et al., Japanese Patent Application KOKOKU No. 56-23587); (3) method using polyethylene glycol mono-alkyl ether aldehydes (Fujino et al., Japanese Patent Application KOKAI No. 61-178926); (4) method for introducing polyethylene glycol mono-alkyl ethers into amino groups of protein via imidoyl groups (Fujino et al., Japanese Patent Application KOKAI No. 63-10800); (5) method using polyethylene glycol mono-alkyl ethers and N-hydroxysuccinimide [Leonard, M., et al., Tetrahedron, 40, 1581-1584 (1984) Abuchowski, A. et al., Cancer Biochem Biophys., 7, 175 (1984)]; (6) method for introducing single chain polyethylene glycol mono-alkyl ethers into amino groups of protein via cyanuric chloride [A. Abuchowski et al., J. Biol. Chem., 252., 3578 (1977)]; (7) method which comprises activating polyethylene glycol mono-alkyl ethers with carbonyldiimidazole and then introducing the activated compounds into amino groups of protein [Charles O.B. Cham, et al., Anal. Biochem., 131, 25 (1983)]; etc. Among these methods, the method (1) is concerned with modification method for introducing compounds represented by the following formula (I):

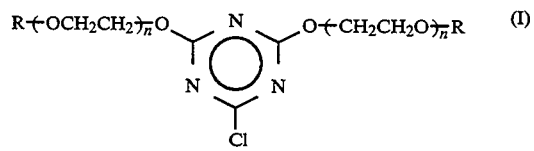

[wherein R represents an alkyl group and n represents an optionally variable positive integer], which are derived from polyethylene glycol mono-alkyl ethers and cyanuric chloride, into amino groups and is characterized in that two polyethylene glycol chains can be introduced into one amino group, unlike other methods for modification (methods (2) through (7) described above). As modified protein according to this modification method, there are known asparaginase [Inada et al., Japanese Patent Application KOKOKU No. 61-42558; Inada et al., Chemistry Letters, 773 (1980); Inada et al., Japanese Journal of Cancer Research, 77, 1264 (1986)], superoxide dismutase Miyata et al., Japanese Patent Application KOKAI No. 2-115280]; and the like. Modified protein obtained using compounds represented by the following formula (III):

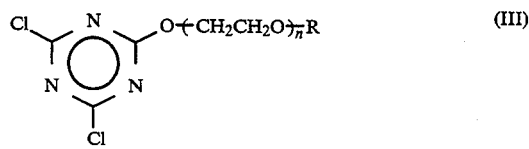

[wherein R and n have the same significances as described above] was compared with modified protein obtained using compounds represented by formula (I). The comparison reveals that modification using compounds represented by formula (I) is more excellent in reducing the antigenicity and retaining the activity.

Now, a protein modifier having high purity is required for preparing modified protein. It was attempted to synthesize Compound (I) which is a protein modifier according to the method (1) recited in the publications supra. However, analysis by high performance gel filtration chromatography reveals that the reaction product was a mixture containing Compound (I) in any case. That is, in the attempt to obtain Compound (I) having a mean molecular weight of 10,000 using a polyethylene glycol mono-alkyl ether having a mean molecular weight of 5,000 and cyanuric chloride; (a) according to the method described in Japanese Patent Application KOKOKU No. 61-42558, 20 g of monomethoxypolyethylene glycol having a molecular weight of 5,000 was dissolved in 100 ml of anhydrous benzene containing 10 g of anhydrous sodium carbonate, the solution was refluxed at 80° C. for 30 minutes, 365 mg of 2,4,6-trichloro-s-triazine was then added to the reaction mixture to react them while refluxing at 80° C. for 24 hours, the reaction residue was filtered off, 300 ml of petroleum ether was added to cause precipitation and the precipitates were washed with petroleum ether several times. Further (b) according to the method described in Japanese Patent Application KOKAI No. 62-115280, 730 mg of cyanuric chloride was added to a mixture of 40 g of polyethylene glycol monomethyl ether (having a mean molecular weight of 5,000), 200 ml of benzene, 20 g of anhydrous sodium carbonate and 10 g of molecular sieve 3A; the resulting mixture was reacted at 80° C. for 20 hours, and then the procedures of adding 400 ml of petroleum ether to the reaction mixture to cause precipitation, dissolving the precipitates in benzene and precipitating again with petroleum ether were repeated 3 times. In both of the methods (a) and (b), there was obtained a mixture of several compounds including Compound (III) ($R=CH_3$) as the main product which have molecular weights over a wide range of from 5,000 to high molecular region (FIGS. 2 and 3). Furthermore, according to the method described in Chemistry Letters, 773 (1980), 730 mg of cyanuric chloride was added to a mixture of 40 g of polyethylene glycol monomethyl ether (a mean molecular weight of 5,000), 200 ml of benzene, 20 g of anhydrous sodium carbonate and 10 g of molecular sieve 3A; the resulting mixture was reacted at 80° C. for 44 hours, and the procedures of precipitating with 400 ml of petroleum ether, dissolving the precipitates in benzene and precipitating again with petroleum ether were repeated 6 times to obtain a mixture of Compound (III) ($R=CH_3$), Compound (I) ($R=CH_3$) and compounds possessing higher molecular weight (FIG. 4). Still further according to the method described in Japanese Journal of Cancer Research, 77, 1264 (1986), 1.12 g of cyanuric chloride was added to a mixture of 60 g of polyethylene glycol monomethyl ether, 200 ml of anhydrous benzene, 20 g of anhydrous sodium carbonate and 20 g of molecular sieve 4A; the resulting mixture was reacted at 80° C. for 120 hours, benzene was distilled off, and then the procedures of dissolving the residue in acetone and precipitating with petroleum ether were repeated 3 times to obtain a mixture of various compounds which mainly contained the products with higher molecular weight (FIG. 5). It is also mentioned in this journal that gel filtration chromatography was carried out on Sephadex G-100 as a carrier to obtain the pure product showing a single peak, which is corresponded to the molecular weight of 10,000, in this chromatography, indicating that homogeneous Compound (I) ($R=CH_3$) was obtained. However, high performance gel filtration chromatography having an excellent separation ability as compared to low speed gel filtration chromatography using Sephadex G-100 or the like as a carrier has been recently developed and as the result, separation which was impossible in the past became possible [Seikagaku, 56, 1481 (1984)]. That is, analysis by means of low speed gel filtration chromatography using Sephadex G-100 or the like as a carrier is insufficient for analysis of purity. In fact, according to the method described in this journal, gel filtration chromatography was performed on Sephadex G-100, and the resulting part, which was the main peak in this chromatography, corresponded to the peak showing a molecular weight of 10,000 in this journal and showed a single peak on gel filtration chromatography using Sephadex G-100 as carrier, was further analyzed by high performance gel filtration chromatography. The result showed that this part was a mixture of various compounds with the major compounds being those with higher molecular weight (FIG. 6).

It is the actual situation that it has been unsuccessful so far to obtain the desired Compound (I) efficiently from such a mixture containing various compounds having molecular weights over a wide range by means of industrial separation and purification (recrystallization, reprecipitation, ultrafiltration, etc.).

On the other hand, where protein is modified using such a mixture containing various compounds having molecular weights over a wide range, the modified protein is not uniform in quality. It is thus extremely difficult to obtain the product having constant quality. In case that such protein is used as a therapeutic agent, various problems such as side effects, etc. might be caused due to impurities.

SUMMARY OF THE INVENTION

An object of the present invention is to provide the compounds represented by formula (I) which are of high purity.

Another object of the present invention is to provide a novel process for preparing the desired compounds represented by formula (I).

A further object of the present invention is to provide protein modified by the high purity compounds represented by formula (I) which maintain the properties of the modified protein such as prolonged plasma half life minimized immunogenicity, etc. and retain the physiological activities and other properties possessed by intact protein as they are.

As a result of extensive investigations, we, the present inventors, have succeeded in obtaining Compound (I) having high purity and, after continuous investigations, we have found that useful protein having pharmacological activities and other protein can be extremely easily modified by high purity Compound (I) and such protein modified by high purity Compound (I) guarantees uniform quality, possesses properties of modified protein such as prolonged plasma half life, minimized immunogenicity, good solubility in an organic solvent, etc. and still retains the physiological activities and other properties possessed by unmodified protein as they are.

That is, a first aspect of the present invention is to provide high purity polyethylene glycol derivatives represented by formula (I):

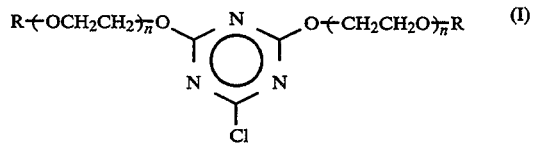

[wherein R represents an alkyl group and n represents an optionally variable positive integer], namely, high purity Compound (I). The present invention also provides Compound (I) showing purity of 75% or more in terms of high performance gel filtration chromatography. The present invention further provides high purity Compound (I) which can be prepared by reacting Compound (II) represented by the following formula (II):

[wherein R and n have the same significances as defined above] with cyanuric chloride in the presence of a metal compound belonging to Group IIB and which contain scarcely by-products with higher molecular weight and by-products such as Compound (III) represented by formula:

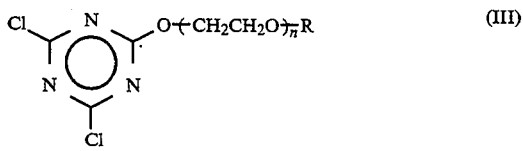

[wherein R and n have the same significances as defined above] produced by reacting Compound (II) with cyanuric chloride in a 1:1 molar ratio, or other by-products etc.

A second aspect of the present invention relates to a process for preparing Compound (I) which comprises reacting Compound (II) with cyanuric chloride in the presence of a metal compound belonging to Group IIB.

A third aspect of the present invention lies in providing modified protein with the high purity Compound (I).

BRIEF DESCRIPTION OF THE DRAWINGS

FIG. 6 shows high performance gel filtration chromatography of a polyethylene glycol derivative which was synthesized and then purified according to the method described in Japanese Journal of Cancer Research, 77, 1264 (1986).

DETAILED DESCRIPTION OF THE PREFERRED EMBODIMENTS

Figure 1:
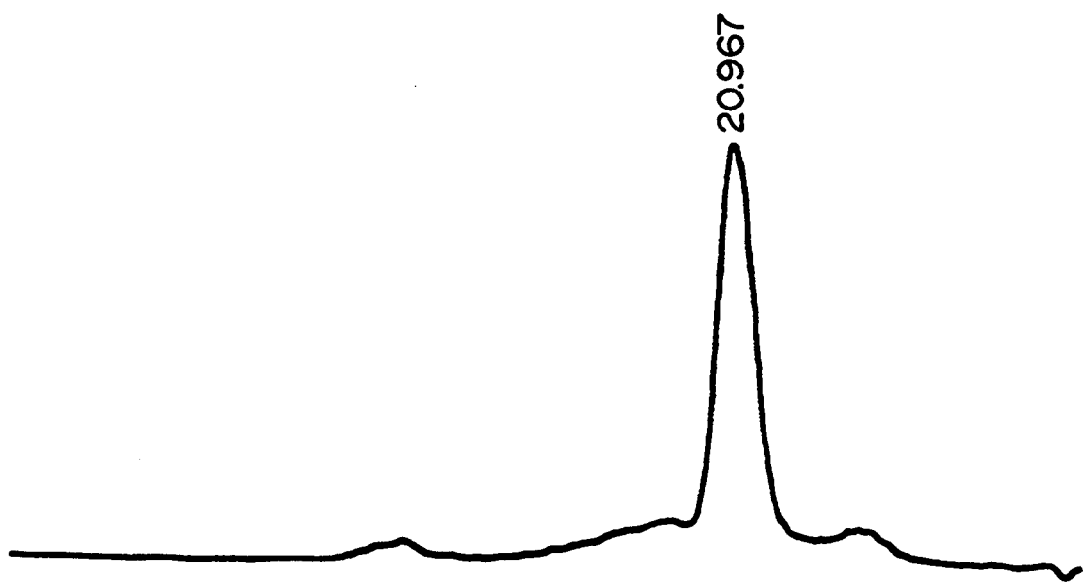
FIG. 1 shows high performance gel filtration chromatography of a high purity polyethylene glycol derivative obtained by the method of Example 1.
Figure 2:
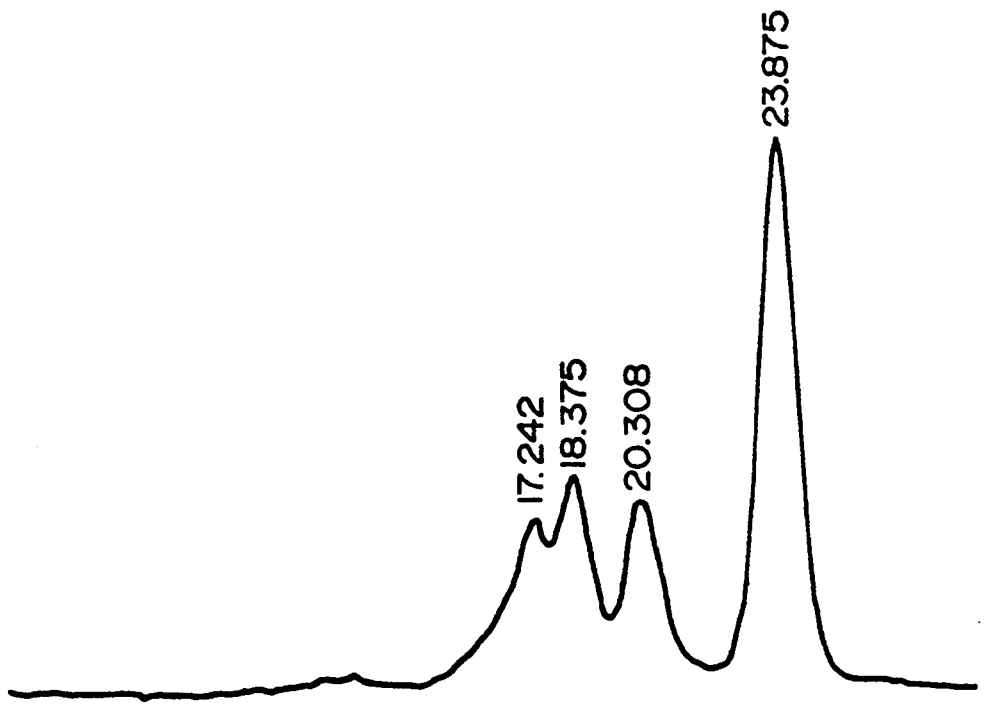
FIG. 2 shows high performance gel filtration chromatography of a polyethylene glycol derivative obtained by the method described in Japanese Patent Application KOKOKU No. 61-42558.
Figure 3:
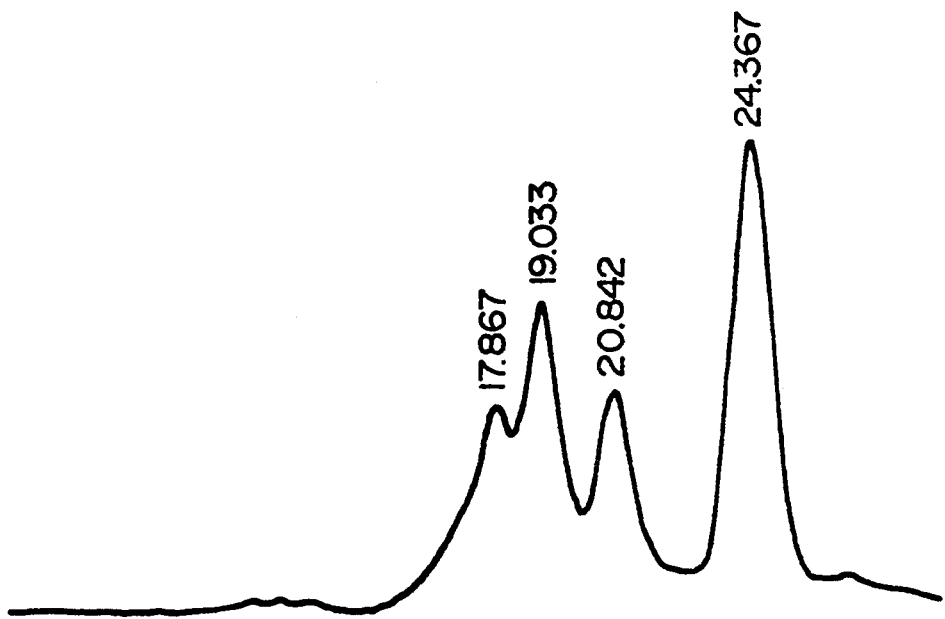
FIG. 3 shows high performance gel filtration chromatography of a polyethylene glycol derivative obtained by the method described in Japanese Patent Application KOKAI No. 62-115280.
Figure 4:
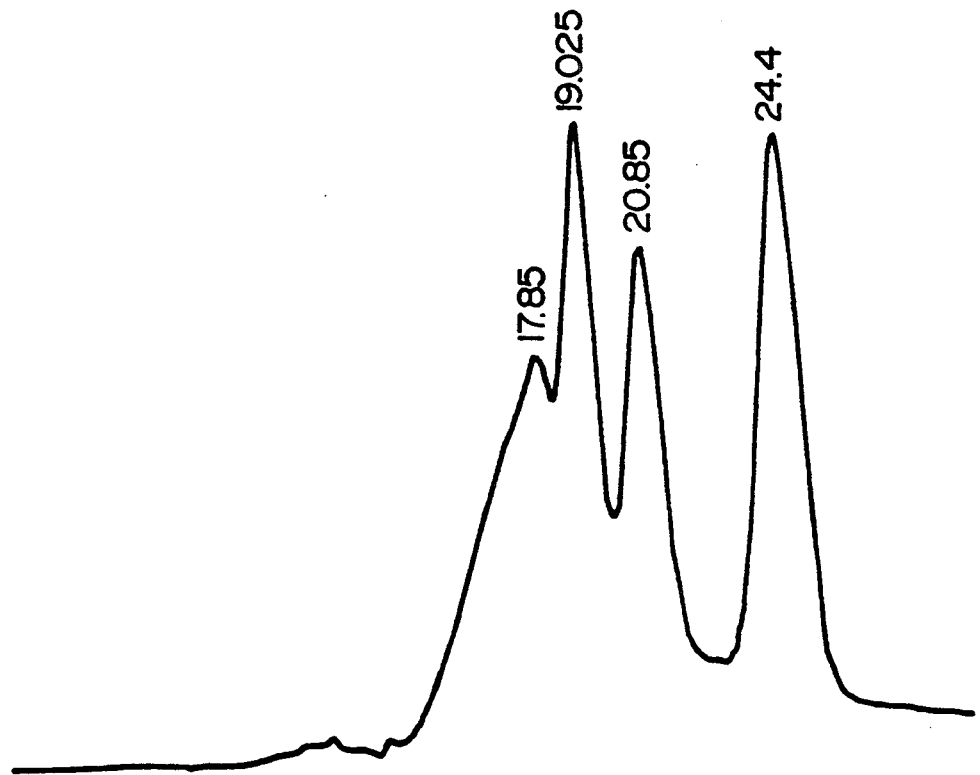
FIG. 4 shows high performance gel filtration chromatography of a polyethylene glycol derivative obtained by the method described in Chemistry Letters, (1980).
Figure 5:
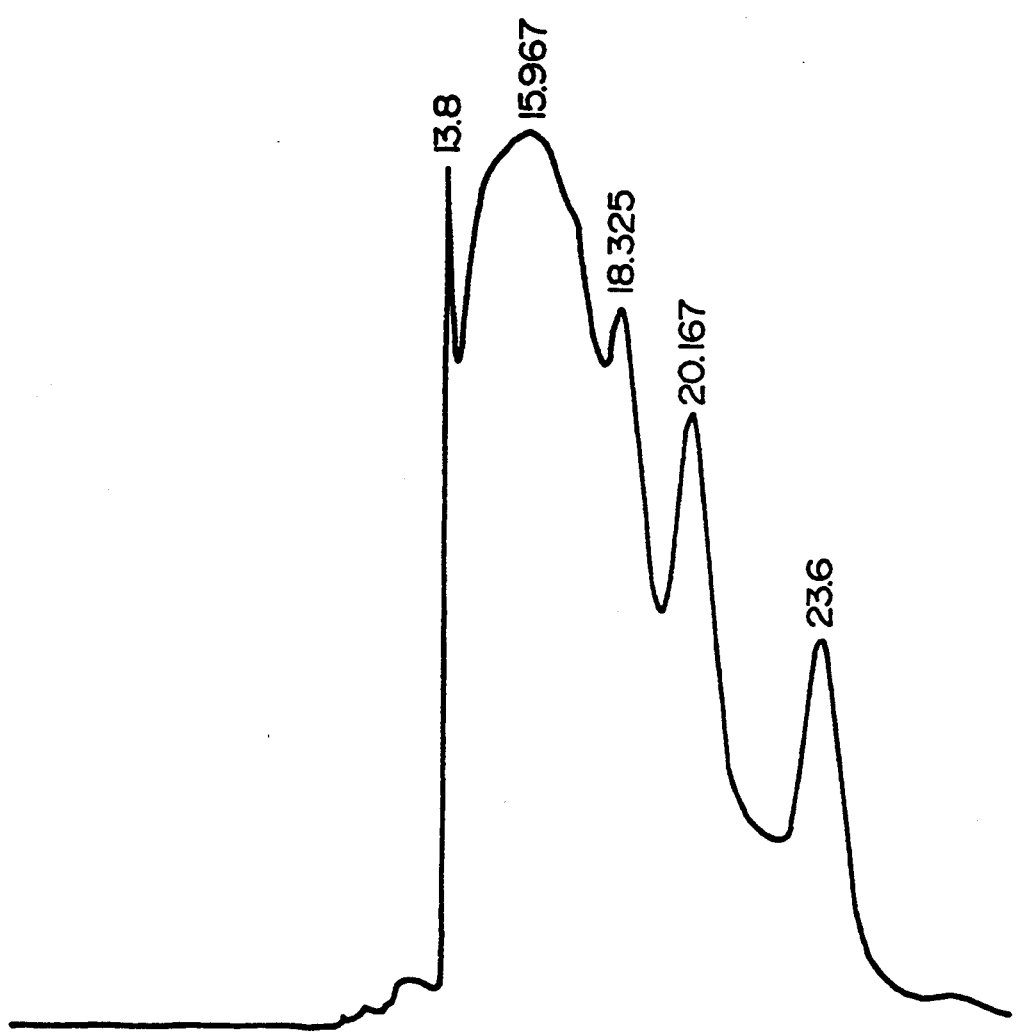
FIG. 5 shows high performance gel filtration chromatography of a polyethylene glycol derivative obtained by the method described in Japanese Journal of Cancer Research, 77, 1264 (1986).

The modified protein of the present invention is represented by formula:

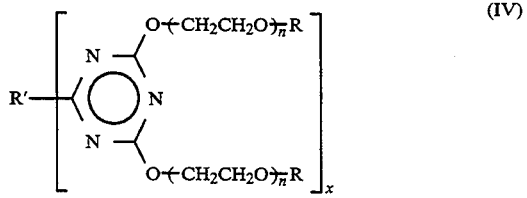

[wherein R and n have the same significances as defined above; R' represents protein containing an amino group and x represents an optionally variable positive integer].

In the formulae above, the alkyl group shown by R is preferably an alkyl group having 1 to 18 carbon atoms.

Examples of the alkyl group include methyl, ethyl, n-propyl, isopropyl, n-butyl, isobutyl, sec-butyl, n-pentyl, isopentyl, n-hexyl, isohexyl, n-octyl, n-nonyl, isononyl, n-decyl, isodecyl, n-undecyl, n-dodecyl, n-tridecyl, n-tetradecyl, n-hexadecyl, n-heptadecyl, n-octadecyl, etc. Of these, those having 1 to 4 carbon atoms are particularly preferred, with the most preference being methyl.

In the formulae above, the positive integer shown by n is preferably 10 to 700, more preferably 50 to 350.

In formula (IV), R' represents protein containing an amino group. The protein may be any of protein derived from various animals including human, microorganisms, plants, genetically engineered products and synthesized products. Examples of such protein include cytokinin [e.g., various interferons (interferon-α, interferon-β, interferon-γ), interleukin-2, interleukin-3, etc.], hormones [e.g., insulin, growth hormone releasing factor (GRF), calcitonin, calcitonin gene-related peptide (CGRP), atrial natriuretic peptide (ANP), vasopressin, corticotropin releasing factor (CRF), vasoactive intestinal peptide (VIP), secretin, α-melanocyte stimulating hormone (α-MSH), adrenocorticotropic hormone (ACTH), cholecystokinin (CCK), glucagon, parathyroid hormone (PTH), parathyroid hormone-related protein (PTHrp), somatostatin, enkephalin, endothelin, substance P, dynorphin, oxytocin, growth hormone releasing peptide (GHRP, e.g., cf. Endocrinology, 114, 1537 (1984), etc.], growth factors [e.g., growth hormone (GH), insulin-like growth factor (IGF-I, IGF-II), β-nerve growth factor (β-NGF), basic fibroblast growth factor (bFGF), transforming growth factor-β(TGF-β), erythropoietin, granulocyte colony stimulating factor (G-CSF), granulocyte macrophage colony stimulating factor (GM-CSF), platelet-derived growth factor (PDGF), epidermal growth factor (EGF), etc.], enzymes [e.g., tissue plasminogen activator (t-PA), elastase, superoxide dismutase (SOD), bilirubin oxidase, catalase, uricase, urokinase, thermolysin, trypsin, chymotrypsin, V8 protease, chondroitin ABC lyase, asparaginase, etc.], other protein [e.g., ubiquitin, islet-activating protein (IAP), serum thymic factor (STF), peptide-T, albumin, globulin, transferrin, lipoprotein, lipid A derivatives, house dust mite protein, trypsin inhibitor, etc.] and derivatives thereof.

In formula (IV), x is an optionally variable positive integer but does not exceed the number of amino groups present in the protein to be modified.

The high purity Compound (I) described above can be prepared, for example, as follows.

That is, Compound (I) can be prepared by reacting Compound (II) with cyanuric chloride in an appropriate solvent in the presence of the metal compound of Group IIB. A reaction time is generally in the range of from 1 to 300 hours and a reaction temperature is generally in the range of from 50° to 140° C., preferably approximately 70° to 110° C. The solvent used for the reaction may be any solvent so long as it is inert to the reagents used for the reaction. Examples of the solvent are aromatic hydrocarbon type solvents such as benzene, toluene, etc., and halogenated hydrocarbon type solvents such as 1,2-dichloroethane, etc. The metal compound of Group IIB is preferably oxides of the metal of Group IIB such as zinc oxide,. cadmium oxide, mercury oxide. It is also desired to remove water from the reaction system. For this purpose, for example, molecular sieve or the like may be used.

The purity of the high purity polyethylene glycol derivative obtained by the present invention is determined by high performance gel filtration chromatography under the following conditions.

Conditions:

| | |
|---|---|
| Column: | TSK-gel G3000SW 7.5 mmφ × 60 cm (manufactured by TOSO Co., Ltd.) |
| Eluant: | ethanol/[0.01 M phosphate buffer (pH 7) + 0.2 M aqueous sodium chloride solution] = 1/19 |
| Flow rate: | 0.7 ml/min |
| Detection wavelength: | 254 nm |

As shown in FIG. 1, the polyethylene glycol derivative according to the present invention has much higher purity than any of those obtained by the prior art (FIGS. 2 to 6). The purity of the polyethylene glycol derivative in accordance with the present invention exceeds 75%, in terms of the area percentage method.

That is, the polyethylene glycol derivative in accordance with the present invention has a purity exceeding 75% by high performance gel filtration chromatography.

Herein the purity by high performance gel filtration chromatography refers to an area percentage of the area of the peak formed by Compound (I) to the area of all peaks formed by the chart of high performance gel filtration chromatography. In general, data processing is performed using a data processor such as Chromatopak C-R6A (Shimadzu), etc.

The reaction product obtained by the process described above is already extremely rich of Compound (I). Thus, the reaction product may be used as Modifier (I) as it is. Where it is desired to obtain Compound (I) of higher purity, the reaction product is further subjected to industrial separation and purification means such as recrystallization, reprecipitation, ultrafiltration, etc.

Chemical modification of protein with the high purity Compound (I) of the present invention can be performed in a conventional manner. That is, the reaction may be carried out in a buffer solution of boric acid, phosphoric acid, acetic acid, etc. showing pH of approximately 8 to 10 at a temperature below room temperature for about 1 to about 72 hours. The amount of employed modifier is variable, depending upon the desired degree of modification. If necessary and desired, the reaction solution may be purified by ordinary means conventionally used for purification of protein such as dialysis, salting out, ultrafiltration, gel filtration chromatography, ion exchange chromatography, hydrophobic chromatography, reverse phase chromatography, affinity chromatography, electrophoresis, etc. Thus, the desired modified protein can be obtained.

Compound (I) of high purity in accordance with the present invention is useful for modification of protein for the purpose of decreasing antigenicity, prolonging half life time, improving transfer to tissue, etc. By modifying protein with the high purity Compound (I), the modified protein which has satisfactory quality as a therapeutic agent composition, for example, modified asparaginase, can easily be obtained.

Furthermore, according to the process of the present invention, Compound (I) having high purity as compared to these of the prior art can be prepared as described above.

The modified protein of the present invention is orally or parenterally administered to mammalian (for example, cow, horse, pig, sheep, human, etc.) in the form of pharmaceutical preparations (e.g., capsules, injections, etc.) comprising suitable drug components, together with conventional carriers, diluents, etc.

Upon administration, for example, where the modified tissue plasminogen activator obtained in Example 46 is administered for the treatment of myocardial infraction, the drug is administered generally in a dose of 1 to 100 mg once a day or by dividing into several portions.

Further where the modified protein is modified hydrolase, synthesis reaction can be effectively carried out using the enzyme.

Hereafter the present invention is described in more detail by referring to examples and test examples but is not deemed to be limited to these examples.

In the following description, each abbreviation means the following.

| | |
|---|---|
| Asx: aspartic acid or asparagine | |
| Glx: glutamic acid or glutamine | |
| Ser: serine | Gly: glycine |
| His: histidine | Arg: arginine |
| Thr: threonine | Ala: alanine |
| Pro: proline | Tyr: tyrosine |
| Val: valine | Met: methionine |
| Ile: isoleucine | Leu: leucine |
| Phe: phenylalanine | Lys: lysine |
| TFA: trifluoroacetic acid | |
| Z: carbobenzoxy | |
| HPLC: high performance liquid chromatography | |
| Bz: benzoyl | |

EXAMPLE 1

Preparation of 2,4-bis-methoxypolyethylene glycol-6-chloro-s-triazine (PEG2)

A mixture of 110 g of polyethylene glycol monomethyl ether having a mean molecular weight of 5,000 and 25 g of molecular sieve 4A was refluxed in 0.5 l of benzene for 6 hours at 80° C. After cooling to room temperature, 50 g of zinc oxide and 1.85 g of cyanuric chloride were added-to the reaction mixture followed by heating at 80° C. to reflux for 53 hours. After cooling to room temperature, 0.5 l of benzene was added to the reaction mixture. After filtering, the filtrate was concentrated to dryness to give 108 g of PEG2 which was one of Compound (I).

Physical Property

High performance gel filtration chromatography
  Column: TSK-gel G3000SW 7.5 mmφ×60 cm (manufactured by TOSO Co., Ltd.)
  Eluant: ethanol/[0.01M phosphate buffer (pH 7)+0.2M aqueous sodium chloride solution]=1/19
  Flow rate: 0.7 ml/min
  Detection wavelength 254 nm
  Retention time: 20,967 minutes
  Purity: 91.5% (area percentage method)
  Chart: as shown in FIG. 1
Silica gel thin layer chromatography
  Silica gel: Kiesel gel 60 (manufactured by Merck Inc.)
  Developing solvent: methylene chloride/methanol=15/2
  Rf value: 0.5

EXAMPLE 2

Preparation of 2,4-bis-methoxypolyethylene glycol-6-chloro-s-triazine (PEG2)

After 11 g of polyethylene glycol monomethyl ether having a mean molecular weight of 5,000 was heated in 50 ml of benzene to reflux for 4 hours at 80° C., the mixture was allowed to cool to room temperature. Then 2.5 g of molecular sieve 4A was added thereto followed by heating at 80° C. for 4 hours to reflux. After allowing to cool to room temperature, 13.5 g of mercury oxide (yellow) and 184 mg of cyanuric chloride were added to the mixture followed by heating at 80° C. to reflux for 27 hours. After cooling to room temperature, 50 ml of benzene was added to the reaction mixture. After centrifugation, benzene was distilled off and the residue was dried to give 9.79 g of PEG2 which was one of Compound (I) (purity of 78.2% in high performance gel filtration chromatography using TSK-gel G3000SW).

EXAMPLE 3

Preparation of 2,4-bis-methoxypolyethylene glycol-6-chloro-s-triazine (PEG2)

After 11 g of polyethylene glycol monomethyl ether having a mean molecular weight of 5,000 was heated to reflux in 50 ml of benzene for 4 hours at 80° C., the mixture was allowed to cool to room temperature. Then 2.5 g of molecular sieve 4A was added thereto followed by heating at 80° C. for 4 hours to reflux. After allowing to cool to room temperature, 7.8 g of cadmium oxide and 184 mg of cyanuric chloride were added to the mixture followed by heating at 80° C. to reflux for 34 hours. After cooling to room temperature, 50 ml of benzene was added to the reaction mixture. After centrifugation, benzene was distilled off and the residue was dried to give 9.35 g of PEG2 which was one of Compound (I) (purity of 78.5% in high performance gel filtration chromatography using TSK-gel G3000SW).

EXAMPLE 4

Purification of 2,4-bis-methoxypolyethylene glycol-6-chloro-s-triazine (PEG2) by gel filtration After 800 mg of the reaction product obtained in Example 1 was dissolved in 20 ml of water, the solution was purified by gel filtration using TSK-gel G3000SW (21.5 mm$\phi$×600 mm, eluted with water). The fraction containing the desired product was freeze dried to give 324 mg of more purified PEG2 which was one of Compound (I) (purity of 99.6% in high performance gel filtration chromatography using TSK-gel G3000SW).

Physical property:
Melting point: 56°–58° C.
Elemental analysis: C 53.65 (54.17), H 8.99 (9.05), N 0.46 (0.41), C 10.33 (0.35).

Data within parenthesis indicates calculated data when the molecular weight of polyethylene glycol monomethyl ether was made 5004.

$^{13}$C-NMR (CDCl$_3$, complete decoupling) δ: 58.6, 67.9, 68.2, 69.7, 69.9, 70.1, 70.3, 70.6, 71.5, 171.6, 172.1.

EXAMPLE 5

Preparation of PEG2-modified papain (PEG2-Pa)

After 45 mg of papain was dissolved in 9 ml of 0.2M acetate buffer (pH 4.5), 0.9 g of PEG2 was added to the solution. The pH of this solution was increased to 10 with 0.1N sodium hydroxide followed by reacting at 28° C. for an hour. The reaction was discontinued by adding 200 ml of chilled 0.2M acetate buffer (pH 6.25) to the reaction solution. After an excess of PEG2 was removed using a ultrafiltration apparatus (for cutting a molecular weight of 30,000), the filtrate was dialyzed to a solution containing 0.1 mM EDTA and 1 mM dithiothreitol (DTT).

Degree of modification: 37.4%.
Activity: 19.7 U/mg protein (70.3%) (one unit hydrolyzes 1.0 μmol of Nα-benzoyl-L-arginine ethyl ester (BAEE) at pH 6.2 and 25° C. for one minute.).

EXAMPLE 6

Preparation of PEG2-modified chymotrypsin (PEG2-Ch)

After 1 g of α-chymotrypsinogen was dissolved in 840 ml of 0.1M borate buffer (pH 10.0), the solution was cooled to 4° C. To the solution was added 24.2 g of PEG2 over an hour. The mixture was reacted at 4° C. for 20 hours. The reaction solution was neutralized with 0.1N hydrochloric acid and an excess of PEG2 was removed using a a ultrafiltration apparatus (for cutting a molecular weight of 30,000). By this reaction, 27% of the amino groups were modified according to the trinitrobenzenesulfonic acid method. The modified α-chymotrypsinogen was activated by trypsin in a conventional manner and dialyzed to water to give PEG2-Ch.

Modification rate: 27.0%.
Activity: 30.51 U/mg protein (67.8%) (one unit hydrolyzes 1.0 pmol of N-benzoyl-L-tyrosine ethyl ester (BTEE) at pH 7.8 and 25° C. for one minute.).

EXAMPLE 7

Preparation of PEG2-modified thermolysin (PEG2-Th)

After 344 mg of thermolysin was dissolved in 68.8 ml of 0.1M borate buffer (pH 10.0), the solution was cooled to 4° C. To the solution was added 1.1 g of PEG2 over an hour. The mixture was reacted at 4° C. for 17 hours. The reaction solution was neutralized with 0.1N hydrochloric acid and an excess of PEG2 was removed using a a ultrafiltration apparatus (for cutting a molecular weight of 30,000) to prepare the product. By this reaction, 26.9% of the amino groups were modified.

Degree of modification: 26.9%.
Activity: 4970 U/mg protein (71.0%) (one unit hydrolyzes milk casein at pH 7.2 and 35° C. for one minute to produce 1.0 μg of tyrosine.)

EXAMPLE 8

PEG2-modified enzymes shown in Table 1 were synthesized by the procedures similar to Examples 1 through 3.

TABLE 1

| List of PEG2-Modified Enzyme | | | | |
|---|---|---|---|---|
| Modified Enzyme | Degree of Modification (%) | Activity (U/mg protein) (% *1) | Solubility (mg/ml MeOH) | Comment |
| PEG2-papain | 48.7 | 7.6 (27.0) | >10 | Papain (papaya latex), MW23406, 28.0 U/mg protein |
| PEG2-trypsin | 23.3 | 7110.0 (71.1) | >10 | Trypsin (bovine pancreas), MW 23300, 10000 U/mg protein |
| | 54.6 | 1930.0 (19.3) | >10 | |

TABLE 1-continued

List of PEG2-Modified Enzyme

| Modified Enzyme | Degree of Modification (%) | Activity (U/mg protein) (% *1) | Solubility (mg/ml MeOH) | Comment |
|---|---|---|---|---|
| PEG2-chymotrypsin | 63.6 | 9.9 (22.0) | >10 | Chymotrypsin (bovine pancreas) MW 26000, 45 U/mg protein |
| PEG2-pepsin | 20.2<br>42.2 | 2491.5 (75.5)<br>1141.8 (34.6) | >10<br>>10 | Pepsin (pig gastric mucous membrane), MW 34644, 3300 U/mg protein |
| PEG2-thermolysin | 52.7 | 2114 (30.2) | >10 | Thermolysin (Bacillus thermoproteaolyticus), MW 34600, 7000 U/mg protein |
| PEG2-V8 | 22.2 | 306 (68.0) | >10 | V8 (Staphylococcus aureus V8), MW 27700, 450 U/mg |

*1:PEG2-papain One unit hydrolyzes 1.0 μmol of Nα-benzoyl-L-arginine ethyl ester (BAEE) at pH 6.2 and 25° C. for one minute.
PEG2-trypsin One BAEE unit = using BAEE as substrate at pH 7.6 and 25° C., one unit produces 0.001ΔA$_{253}$ for one minute.
PEG2-chymotrypsin One unit hydrolyzes 1.0 μmol of Nα-benzoyl-L-tyrosine ethyl ester (BTEE) at pH 7.8 and 25° C. for one minute.
PEG2-pepsin When measured as TCA-soluble product using hemoglobin as substrate, one unit produces 0.001ΔA$_{288}$ for one minute at pH of 2.0 and 37° C.
PEG2-thermolysin One unit hydrolyzes milk casein to produce 1.0 μg of tyrosine at pH of 7.2 and 35° C. for one minute.
PEG2-V8 When measured as TCA-soluble product using casein as substrate, one unit produces 0.001ΔA$_{288}$ for one minute at pH of 7.8 and 37° C.

EXAMPLE 9

Synthesis of peptide using PEG2-modified enzyme 1 mM each of N-protected amino acid and C-protected amino acid was dissolved in a buffer solution (which may also contain an organic solvent) and PEG2-modified enzyme was added to the solution. The mixture was reacted at 20° to 50° C. overnight. When crystals precipitated in the reaction solution, water was added thereto and the crystals were taken by filtration. When no crystals were formed, the reaction solution was concentrated and extraction was performed with ethyl acetate. The ethyl acetate phase was concentrated and ether, hexane or the like was added to the residue to solidify and give the reaction product. Thus the products described in Table 2 were obtained using various PEG2-modified enzymes.

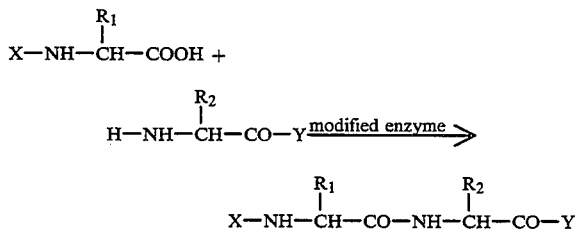

(wherein X and Y each represents a protective group).

TABLE 2

| Product | Melting Point °C. | Yield % | Modified Enzyme |
|---|---|---|---|
| Bz—Arg—Phe—NH2 | 132–134 | 73.8 | trypsin |
| Z—Phe—Tyr—NH2 | 225–228 | 85.3 | chymotrypsin |
| Z—Phe—Val—OBzl | 101–102 | 88.4 | papain |
| Z—Leu—Ile—OMe | 69–72 | 88.0 | thermolysin |

Notes)
Z: carbobenzoxy
NH$_2$: amide
OMe: methyl ester
Bz: benzoyl
OBzl: benzyl ester

EXAMPLE 10

PEG2-modified human insulin (PEG2-human insulin)

In 2 ml of 0.1M borate buffer (pH of 9.5) was dissolved 10 mg of human insulin and, 400 mg of PEG2 was added to the solution. After stirring overnight, pH of the mixture was adjusted to 7.0. After the unreacted PEG2 was removed by passing through Sephadex G-50, water was added to the system and the mixture was concentrated to the whole volume of 2 ml through a ultrafiltering membrane for cutting a molecular weight of 10,000 cut. The concentrate was stored in a freezing room. After a part of the concentrate was freeze dried, it was subjected to elemental analysis to determine a rate of its carbon to the nitrogen (N/C×100) (hereafter referred to as N/C value): N/C value=6.5.

Assay for PEG2-human insulin

Human insulin and PEG2-human insulin containing the same amount of human insulin were injected to rabbit for test and its blood sugar level was determined by the glucostat method of Washington Biochemical Company in Freehold City, N.J. The results are shown in Table 3.

TABLE 3

| | Glucose Level in Blood 3 Hours After |
|---|---|
| PEG2-human insulin | 50% of normal level |
| Human insulin | 20% of normal level |

EXAMPLE 11

PEG2-modified human insulin

To 280 μl of 0.05M borate buffer (pH 10) containing 0.42 mg of insulin (human) was added 8.6 mg of high purity PEG2 prepared in Example 1 at 4° C. and the resulting mixture was allowed to stand at 4° C. Further 6.5 hours after, 2.9 mg of PEG2 was added to the mixture, which was allowed to stand at 4° C. for 29 hours. After neutralizing with 0.1M acetic acid, purification was performed by reverse phase high performance liquid chromatography [YMC-ODS, 4.6 mmφ×250 mm; gradient using eluant A=water-containing 0.1% TFA and eluant B=acetonitrile (0.1% TFA) (initial concentration of eluant B: 25%, gradient: 1%/min); flow rate: 1 ml/min]. After the fraction containing the product was freeze dried, 200 μl of water was added to give an aqueous solution containing the desired product.

Physical Property

Reverse phase high performance liquid chromatography
  Column: YMC-ODS AM303, 4.6 mmφ×250 mm (manufactured by Yamamura Chemical Co., Ltd.)

Eluant: gradient
  eluant A: water (0.1% trifluoroacetic acid)
  eluant B: acetonitrile (0.1% trifluoroacetic acid)
  initial concentration of eluant B: 25%
  concentration gradient: 1%/min
Flow rate: 1 ml/min
Detection wavelength: 220 nm
Retention time: 25.4 minutes Amino acid analysis in the acid decomposition products (decomposition products after treating with 6N hydrochloric acid-phenol at 110° C. for 24 hours)

Asx 2.5 (3), Glx 5.2 (7), Ser 2.6 (3), Gly 3.4 (4), His 1.5 (2), Arg 0.7 (1), Thr 1.9 (3), Ala* 1 (1), Pro 0.9 (1), Tyr 2.9 (4), Val 2.7 (4), Cys—(6), Ile 1.1 (2), Leu 4.4 (6), Phe 2.2 (3), Lys 0.7 (1)

* standard amino acid; data within parentheses indicate calculated data; symbol—indicates data not measured.

EXAMPLE 12

PEG2-modified elcatonin (PEG2-elcatonin)

In 2 ml of 0.1M borate buffer (pH 9.5) was dissolved 10 mg of elcatonin and, 300 mg of PEG2 was added to the solution. After stirring overnight, pH of the mixture was adjusted to 7.0. The unreacted PEG2 was removed by passing through Sephadex G-50 and water was added to the system. The mixture was concentrated to the whole volume of 2 ml through a ultrafiltering membrane for cutting a molecular weight of 10,000 cut and the concentrate was stored in a freezing room. After a part of the concentrate was freeze dried, it was subjected to elemental analysis to determine its N/C value. N/C value=4.5.

Assay for PEG2-elcatonin

Elcatonin (5 μg/kg) and PEG2-elcatonin (elcatonin content, 5 μg/kg) were intravenously administered to rat at the tail vein. Reduction in blood calcium level in this case was made 100 and a time period until the reduction in blood calcium level reached 50 was measured. The results are shown in Table 4.

TABLE 4

|  | Time period until reduction in blood calcium level reaches 50% |
|---|---|
| PEG2-elcatonin | 72 hours |
| Elcatonin | 48 hours |

Determination of half life of elcatonin blood concentration in rabbit by RIA

Elcatonin (5 μg/kg) and PEG2-elcatonin (elcatonin content, 5 μg/kg) were intravenously administered to rabbit. When its blood concentration 2 minutes after the administration was made 100, the half life was determined. The results are shown in Table 5.

TABLE 5

|  | Half life |
|---|---|
| PEG2-elcatonin | 55 minutes |
| Elcatonin | 10 minutes |

EXAMPLE 13

PEG2-modified human calcitonin

In 180 μl of 0.1M borate buffer was dissolved 0.59 g of human calcitonin and, 6.90 mg of high purity PEG2 prepared in Example 1 was added to the solution at 4° C. The mixture was allowed to stand at 4° C. for 8 hours. After neutralizing with 0.1M acetic acid, purification was performed by reverse phase high performance liquid chromatography [YMC-ODS, 4.6 mmφ×250 mm; gradient using eluant A=water-containing 0.1% TFA and eluant B=acetonitrile (0.1% TFA) (initial concentration of eluant B: 25%, gradient: 1%/min); flow rate: 1 ml/min]. The fraction containing the product was freeze dried to give the desired product.

Physical Property

Reverse phase high performance liquid chromatography
  Column: YMC-ODS AM303, 4.6 mmφ×250 mm (manufactured by Yamamura Chemical Co., Ltd.)
  Eluant: gradient
    eluant A: water (0.1% trifluoroacetic acid)
    eluant B: acetonitrile (0.1% trifluoroacetic acid)
    initial concentration of eluant B: 25%
    concentration gradient: 1%/min
  Flow rate: 1 ml/min
  Detection wavelength: 220 nm
  Retention time: 24.89 minutes Amino acid analysis in the acid decomposition products (decomposition products after treating with 6 N hydrochloric acid-phenol at 110° C. for 24 hours)

Asx 3.3 (3), Glx 2.2 (2), Ser 0.9 (1), Gly 4.3 (4), His 1.0 (1), Thr 5.0 (5), Ala 2.3 (2), Pro 2.1 (2), Tyr 1.0 (1), Val 1.1 (1), Met 0.8 (1), Ile 1.0 (1), Leu* 2 (2), Phe 3.2 (3), Lys 0.9 (1), Cys—(2)

* standard amino acid; data within parentheses indicate calculated data; symbol—indicates data not measured.

EXAMPLE 14

PEG2-peptide shown in Table 6 was obtained in a manner similar to Examples 6 and 8. Furthermore, it was confirmed that the half life of PEG2-peptide blood concentration was prolonged, in the same test as in Example 8 using rabbit (Table 7).

TABLE 6

|  | N/C Value | Number of PEG2 | Molecular Weight |
|---|---|---|---|
| PEG2-insulin | 6.5 | 2 | 28112.6 |
| PEG2-elcatonin | 4.5 | 2 | 25626.8 |
| PEG2-secretin | 8.6 | 1 | 14192 |
| PEG2-VIP | 3.7 | 3 | 36783.3 |
| PEG2-vasopressin | 3.8 | 1 | 12332.7 |
| PEG2-CGRP | 4.2 | 3 | 37246.8 |
| PEG2-enkephalin | 1.8 | 1 | 11708.1 |
| PEG2-hEGF | 5.4 | 3 | 39611.4 |
| PEG2-rEGF | 11.5 | 1 | 16741.7 |
| PEG2-PTHrP (7-34) | 5.5 | 2 | 25669.9 |
| PEG2-CRF | 6.3 | 2 | 27062.5 |
| PEG2-GRF | 7.4 | 2 | 27344.7 |

In the table, hEGF and rEGF mean human EGF and rat EGF, respectively.

Secretin and VIP used in this example are of swine type, and insulin, vasopressin, CGRP, enkephalin, PTHrP (7-34), CRF and GRF are of human type.

TABLE 7

|  | Dose, i.v. (μg/kg) | Half life (minute) |
|---|---|---|
| PEG2-secretin | 5 | 15 |
| Secretin | 5 | 7 |
| PEG2-VIP | 5 | 45 |
| VIP | 5 | 7 |
| PEG2-vasopressin | 2 | 40 |
| Vasopressin | 2 | 18 |

TABLE 7-continued

|  | Dose, i.v. (μg/kg) | Half life (minute) |
| --- | --- | --- |
| PEG2-CGRP | 5 | 55 |
| CGRP | 5 | 10 |
| PEG2-enkephalin | 1 | 25 |
| Enkephalin | 1 | 13 |
| PEG2-hEGF | 10 | 80 |
| hEGF | 10 | 15 |
| PEG2-rEGF | 10 | 45 |
| rEGF | 10 | 15 |
| PEG2-PTHrP(7–34) | 5 | 42 |
| PTHrP(7–34) | 5 | 7 |
| PEG2-CRF | 5 | 54 |
| CRF | 5 | 8 |
| PEG2-GRF | 10 | 60 |
| GRF | 10 | 10 |

Antibody to secretion used is the product of Daiichi Radio Isotope Co., Ltd.; antibodies to calcitonin, VIP, arginine vasopression CGRP, enkephalin, PTHrP (7-34), CRF and GRF used are the products of Peninsula Co., Ltd.; and antibodies to rEGF and hEGF used are the products of Otsuka Assay Co., Ltd.

EXAMPLE 15

PEG2-modified human[ArgS]-vasopressin

In 450 μl of 0.1M borate buffer (pH 10) was dissolved 0.55 mg of human [ArgS]-vasopressin and, 20.0 mg of high purity PEG2 prepared in Example 1 was added to the solution at 4° C. The mixture was allowed to stand at 4° C. for 25.5 hours. After neutralizing with 0.1M acetic acid, purification was performed by reverse phase high performance liquid chromatography [YMC-ODS, 4.6 mmφ×250 mm; gradient using eluant A=water-containing 0.1% TFA and eluant B=acetonitrile (0.1% TFA) (initial concentration of eluant B: 25%, gradient: min); flow rate: 1 ml/min]. The fraction containing the product was freeze dried to give the desired product.

Physical Property

Reverse phase high performance liquid chromatography
  Column: YMC-ODS AM303, 4.6 mmφ×250 nun (manufactured by Yamamura Chemical Co., Ltd.)
  Eluant: gradient
    eluant A: water (0.1% trifluoroacetic acid)
    eluant B: acetonitrile (0.1% trifluoroacetic acid)
    initial concentration of eluant B: 25%
    concentration gradient: 1%/min
    Flow rate: 1 ml/min
    Detection wavelength: 220 nm
    Retention time: 25.00 minutes
Amino acid analysis in the acid decomposition products (decomposition products after treating with 6N hydrochloric acid-phenol at 110° C. for 24 hours)
  Asx 0.9 (1), Glx 0.9 (1), Gly 1.0 (1), Arg 0.8 (1), Pro 1.0 (1), Try 1.0 (1), Phe* 1 (1), Cys—(2)
* standard amino acid; data within parentheses indicate calculated data; symbol—indicates data not measured.

EXAMPLE 16

PEG2-modified CGRP

In 300 μl of 0.1M borate buffer (pH 10) was dissolved 1 mg of human CGRP and, 16 mg of high purity PEG2 prepared in example 1 was added to the solution at 4° C. The mixture was allowed to stand at 4° C. for 31 hours. After neutralizing with 0.1M acetic acid, purification was performed by reverse phase high performance liquid chromatography [YMC-ODS, 4.6 mmφ×250 mm; gradient using eluant A=water-containing 0.1% TFA and eluant B=acetonitrile (0.1% TFA) (initial concentration of eluant B: 25%, gradient: 1%/min); flow rate: 1 ml/min]. The fraction containing the product was freeze dried to give the desired product.

Physical Property

Reverse phase high performance liquid chromatography
  Column: YMC-ODS AM303, 4.6 mmφ×250 nun (manufactured by Yamamura Chemical Co., Ltd.)
  Eluant: gradient
    eluant A: water (0.1% trifluoroacetic acid)
    eluant B: acetonitrile (0.1% trifluoroacetic acid)
    initial concentration of eluant B: 25%
    concentration gradient: 1%/min
    Flow rate: 1 ml/min
    Detection wavelength: 220 nm
    Retention time: 21.25 minutes
Amino acid analysis in the acid decomposition products (decomposition products after treating with 6 N hydrochloric acid-phenol at 110° C. for 24 hours)
  Asx 3.5 (4), Ser 2.7 (3), Gly 3.8 (4), His 0.9 (1), Arg 1.9 (2), Thr 3.6 (4), Ala* 4 (4), Pro 1.1 (1), val 4.1 (5), Leu 2.8 (3), Phe 1.9 (2), Lys 1.6 (2), Cys—(2)
* standard amino acid; data within parentheses indicate calculated data; symbol—indicates data not measured.

EXAMPLE 17

PEG2-modified mouse EGF (PEG2-mEGF)

To 60 μl of 0.07M borate buffer (pH 10) containing 150 μg of mouse EGF was added 2 mg of high purity PEG2 prepared in Example 1 at 4° C. The mixture was allowed to stand at 4° C. for 30 hours. After neutralizing with 0.5N acetic acid, purification was performed by reverse phase high performance liquid chromatography [YMC-ODS, 4.6 mmφ×250 mm; gradient using eluant A=water-containing 0.1% TFA and eluant B=acetonitrile (0.1% TFA) (initial concentration of eluant B: 25%, gradient: 1%/min); flow rate: 1 ml/min]. The fraction containing the product was freeze dried to give the desired product.

Physical Property

Reverse phase high performance liquid chromatography
  Column: YMC-ODS AM303, 4.6 mmφ×250 mm (manufactured by Yamamura Chemical CO., Ltd.)
  Eluant: gradient
    eluant A: water (0.1% trifluoroacetic acid)
    eluant B: acetonitrile (0.1% trifluoroacetic acid)
    initial concentration of eluant B: 25%
    concentration gradient: 1%/min
    Flow rate: 1 ml/min
    Detection wavelength: 220 nm
    Retention time: 20.73 minutes
Amino acid analysis in the acid decomposition products (decomposition products after treating with 6 N hydrochloric acid-phenol at 110° C. for 24 hours)
  Asx 5.3 (7), Glx 2.8 (3), Set 5.4 (6), Gly 5.9 (6), His 0.9 (1), Arg 3.4 (4), Thr 1.9 (2), Pro 2.0 (2), Tyr 4.4 (5), Val 1.6 (2), Met 0.4 (1), Ile 1.5 (2), Leu* 4 (4), Cys—(6), Trp—(2)
* standard amino acid; data within parentheses indicate calculated data; symbol—indicates data not measured.

EXAMPLE 18

PEG2-modified human GRF(1-44)NH₂

In 2 ml of 0.1M borate buffer (pH 10) was dissolved 5 mg of human GRF(1-44)NH$_2$ and, 59.5 mg of high purity PEG2 prepared in Example 1 was added to the solution at 4° C. The mixture was allowed to stand at 4° C. for 18 hours. After neutralizing with 0.1M acetic acid, purification was performed by reverse phase high performance liquid chromatography [YMC-ODS, 1 cm$\phi$×30 cm; gradient using eluant A=water-containing 0.1% TFA and eluant B=acetonitrile (0.1% TFA) (initial concentration of eluant B: 32%, gradient: 0.25%/min); flow rate: 3 ml/min]. The 3 fractions containing the Products A, B and C were freeze dried to give 5 mg of Product A, 25 mg of Product B and 14 mg of Product C, respectively.

Physical Property of Product A

Reverse phase high performance liquid chromatography
  Column: YMC-ODS AM303, 4.6 mm$\phi$×250 mm (manufactured by Yamamura Chemical Co., Ltd.)
  Eluant: gradient
    eluant A: water (0.1% trifluoroacetic acid)
    eluant B: acetonitrile (0.1% trifluoroacetic acid)
  initial concentration of eluant B: 32%
  concentration gradient: 0.5%/min
  Flow rate: 1 ml/min
  Detection wavelength: 220 nm
  Retention time: 22.63 minutes
Amino acid analysis in the acid decomposition products (decomposition products after treating with 6 N hydrochloric acid-phenol at 110° C. for 24 hours)
  Asx 3.4 (4), Glx 7.5 (7), Ser 3.5 (4), Gly 2.7 (3), Arg 6.1 (6), Thr 0.9 (1), Ala 4.3 (5), Tyr 2.0 (2), Val 1.0 (1), Met 1.1 (1), Ile 2.1 (2), Leu* 5 (5), Phe 0.9 (1), Lys 2.0 (2)

* standard amino acid; data within parentheses indicate calculated data.

Physical Property of Product B

Reverse phase high performance liquid chromatography
  Column: YMC-ODS AM303, 4.6 mm$\phi$×250 mm (manufactured by Yamamura Chemical Co., Ltd.)
  Eluant: gradient
    eluant A: water (0.1% trifluoroacetic acid)
    eluant B: acetonitrile (0.1% trifluoroacetic acid)
  initial concentration of eluant B: 32%
  concentration gradient: 0.5%/min
  Flow rate: 1 ml/min
  Detection wavelength: 220 nm
  Retention time: 26.25 minutes
Amino acid analysis in the acid decomposition products (decomposition products after treating with 6 N hydrochloric acid-phenol at 110° C. for 24 hours)
  Asx 3.2 (4), Glx 5.8 (7), Ser 3.6 (4), Gly 3.1 (3), Arg 4.8 (6), Thr 0.7 (1), Ala 4.3 (5), Tyr 1.9 (2), Val 1.1 (1), Met 0.3 (1), Ile 2.0 (2), Leu* 5 (5), Phe 0.9 (1), Lys 2.1 (2)

* standard amino acid; data within parentheses indicate calculated data.

Physical Property of Product C

Reverse phase high performance liquid chromatography
  Column: YMC-ODS AM303, 4.6 mm$\phi$×250 mm (manufactured by Yamamura Chemical Co., Ltd.)
  Eluant: gradient
    eluant A: water (0.1% trifluoroacetic acid)
    eluant B: acetonitrile (0.1% trifluoroacetic acid)
  initial concentration of eluant B: 32%
  concentration gradient: 0.5%/min
  Flow rate: 1 ml/min
  Detection wavelength: 220 nm
  Retention time: 28.61 minutes
Amino acid analysis in the acid decomposition products (decomposition products after treating with 6 N hydrochloric acid-phenol at 110° C. for 24 hours)
  Asx 3.0 (4), Glx 6.5 (7), Set 3.6 (4), Gly 2.3 (3), Arg 6.4 (6), Thr 0.8 (1), Ala 4.0 (5), Tyr 2.2 (2), Val 1.2 (1), Met 0.5 (1), Ile 2.3 (2), Leu* 5 (5), Phe 0.9 (1), Lys 2.6 (2)

* standard amino acid; data within parentheses indicate calculated data.

EXAMPLE 19

PEG2-modified human GRF(1-29)NH₂

In 2 ml of 0.1M borate buffer (pH 10) was dissolved 5 mg of human GRF(1-29)NH$_2$ and, 86 mg of high purity PEG2 prepared in Example 1 was added to the solution at 4° C. The mixture was allowed to stand at 4° C. for 20.5 hours. After neutralizing with 0.1M acetic acid, purification was performed by reverse phase high performance liquid chromatography [YMC-ODS, 1 cm$\phi$×30cm; gradient using eluant A=water-containing 0.1% TFA and eluant B=acetonitrile (0.1% TFA) (initial concentration of eluant B: 32%, gradient: 0.25%/min); flow rate: 3 ml/min]. The 4 fractions containing Products A, B, C and D were freeze dried to give 121 μg*/500 μl of Product A, 178 μg*/500 μl of Product B, 472 μg*/500 μl of Product C and 195 μg*/500 μl of Product D, respectively (*: protein content).

Physical Property of Product A

Reverse phase high performance liquid chromatography
  Column: YMC-ODS AM303, 4.6 mm$\phi$×250 mm (manufactured by Yamamura Chemical Co., Ltd.)
  Eluant: gradient
    eluant A: water (0.1% trifluoroacetic acid)
    eluant B: acetonitrile (0.1% trifluoroacetic acid)
  initial concentration of eluant B: 35%
  concentration gradient: 0.5%/min
  Flow rate: 1 ml/min
  Detection wavelength: 220 nm
  Retention time: 19.34 minutes
Amino acid analysis in the acid decomposition products (decomposition products after treating with 6 N hydrochloric acid-phenol at 110° C. for 24 hours)
  Asx 2.5 (3), Glx 1.6 (2), Ser 2.9 (3), Gly 1.3 (1), Arg 3.8 (3), Thr 0.9 (1), Ala 3.2 (3), Tyr 1.2 (2), Val 1.0 (1), Met 0.3 (1), Ile 1.9 (2), Leu* 4 (4), Phe 1.0 (1), Lys 1.9 (2)

* standard amino acid; data within parentheses indicate calculated data.

Physical Property of Product B

Reverse phase high performance liquid chromatography
  Column: YMC-ODS AM303, 4.6 mm$\phi$×250 nun (manufactured by Yamamura Chemical Co., Ltd.)
  Eluant: gradient
    eluant A: water (0.1% trifluoroacetic acid)
    eluant B: acetonitrile (0.1% trifluoroacetic acid)
  initial concentration of eluant B: 35%
  concentration gradient: 0.5%/min
  Flow rate: 1 ml/min Detection wavelength: 220 nm
Retention time: 20.05 minutes
Amino acid analysis in the acid decomposition products (decomposition products after treating with 6N hydrochloric acid-phenol at 110° C. for 24 hours)
Asx 2.5 (3), Glx 1.8 (2), Set 2.9 (3), Gly 1.1 (1), Arg 3.0 (3), Thr 0.9 (1), Ala 3.2 (3), Tyr 2.0 (2), Val 0.9 (1), Met 0.4 (1), Ile 1.9 (2), Leu* 4 (4), Phe 1.0 (1), Lys 1.9 (2)
* standard amino acid; data within parentheses indicate calculated data.

Physical Property of Product C

Reverse phase high performance liquid chromatography
Column: YMC-ODS AM303, 4.6 mm$\phi$×250 mm (manufactured by Yamamura Chemical Co., Ltd.)
Eluant: gradient
eluant A: water (0.1% trifluoroacetic acid)
eluant B: acetonitrile (0.1% trifluoroacetic acid)
initial concentration of eluant B: 35%
concentration gradient: 0.5%/min
Flow rate: 1 ml/min
Detection wavelength: 220 nm
Retention time: 21.72 minutes
Amino acid analysis in the acid decomposition products (decomposition products after treating with 6 N hydrochloric acid-phenol at 110° C. for 24 hours)
Asx 2.5 (3), Glx 1.8 (2), Ser 2.9 (3), Gly 1.1 (1), Arg 3.1 (3), Thr 0.9 (1), Ala 3.3 (3), Tyr 2.0 (2), Val 1.0 (1), Met 0.4 (1), Ile 1.9 (2), Leu* 4 (4), Phe 1.0 (1), Lys 1.7 (2)
* standard amino acid; data within parentheses indicate calculated data.

Physical Property of Product D

Reverse phase high performance liquid chromatography
Column: YMC-ODS AM303, 4.6 mm$\phi$×250 mm (manufactured by Yamamura Chemical Co., Ltd.)
Eluant: gradient
eluant A: water (0.1% trifluoroacetic acid)
eluant B: acetonitrile (0.1% trifluoroacetic acid)
initial concentration of eluant B: 35%
concentration gradient: 0.5%/min
Flow rate: 1 ml/min
Detection wavelength: 220 nm
Retention time: 22.53 minutes
Amino acid analysis in the acid decomposition products (decomposition products after treating with 6 N hydrochloric acid-phenol at 110° C. for 24 hours)
Asx 2.4 (3), Glx 1.9 (2), Ser 2.9 (3), Gly 1.2 (1), Arg 3.1 (3), Thr 0.9 (1), Ala 3.1 (3), Tyr 1.9 (2), Val 1.0 (1), Met 0.1 (1), Ile 1.9 (2), Leu* 4 (4), Phe 1.0 (1), Lys 1.8 (2)
* standard amino acid; data within parentheses indicate calculated data.

EXAMPLE 20

PEG2-modified human interferon α

To 100 μl of 0.1M borate buffer (pH 10) containing 80.4 μg of human interferon a was added 3 mg of high purity PEG2 prepared in Example 1. Further 2 hours and 45 minutes after, 2.5 mg of PEG2 was added to the mixture, which was then allowed to stand for 24 hours (reaction temperature was at 4° C.). Then, purification was performed by gel filtration using TSK G3000SW [7.5 mm$\phi$×600 mm, 0.1M aqueous sodium chloride solution (containing 5% ethanol)]. After the fraction containing the desired product was desalted and freeze dried, 50 μl of water was added to give an aqueous solution containing the product (protein content, 41.3 μg/50 μl ).

Physical Property

High performance gel filtration chromatography:
Column: TSK-gel G3000SW 7.5 mm$\phi$×600 mm (manufactured by TOSO Co., Ltd.)
Eluant: 0.1M aqueous sodium chloride solution (containing 5% ethanol)
Flow rate: 0.6 ml/min
Detection wavelength: 220 nm
Retention time: 15.94 minutes

EXAMPLE 21

PEG2-modified swine α-MSH

In 360 μl of 0.05M borate buffer (pH 10) was dissolved 0.51 mg of a-MSH (swine) and, 12 mg of high purity PEG2 prepared in Example 1 was added to the solution. The mixture was allowed to stand at 4° C. for 16 hours. After neutralizing with 0.1M acetic acid, purification was performed by reverse phase high performance liquid chromatography [YMC-ODS, 4.6 mm$\phi$×250 mm; gradient using eluant A=water-containing 0.1% TFA and eluant B=acetonitrile (0.1% TFA) (initial concentration of eluant B: 30%, gradient: 1%/min); flow rate: 1 ml/min]. After the fraction containing the product was freeze dried, 200 μl of water was added to give the an aqueous solution of the desired product (protein content: 49.2 μg/200 μl ).

Physical Property

Reverse phase high performance liquid chromatography
Column: YMC-ODS AM303, 4.6 mm$\phi$×250 mm (manufactured by Yamamura Chemical Co., Ltd.)
Eluant: gradient
eluant A: water (0.1% trifluoroacetic acid)
eluant B: acetonitrile (0.1% trifluoroacetic acid)
initial concentration of eluant B: 30%
concentration gradient: 1%/min
Flow rate: 1 ml/min
Detection wavelength: 220 nm
Retention time: 18.52 minutes
Amino acid analysis in the acid decomposition products (decomposition products after treating with 6 N hydrochloric acid-phenol at 110° C. for 24 hours)
Glx 0.8 (1), Ser 2.1 (2), Gly 1.1 (1), His 1.0 (1), Arg 1.2 (1), Pro 1.1 (1), Tyr 1.0 (1), Val 1.1 (1), Met 0.3 (1), Phe* 1 (1), Lys 1.0 (1), Trp—(1)
* standard amino acid; data within parentheses indicate calculated data; symbol—indicates data not measured.

EXAMPLE 22

PEG2-modified human ACTH (4-10)

In 130 μl of 0.1M borate buffer (pH 10) was dissolved 0.50 mg of human ACTH (4-10) and, 5.2 mg of high purity PEG2 prepared in Example 1 was added to the solution. Further 5 hours after, 15.6 mg of PEG2 was added and 20.8 mg of PEG2 was further added 2 hours after. The mixture was allowed to stand for 17 hours. Since the reaction was not completed, 135 μl of 0.1M borate buffer (pH 10) was added to the mixture and 20.8 mg of PEG2 was further added, which was allowed to stand for 9 hours (reaction temperature was at 4° C.). After neutralizing with 0.1M acetic acid, purification was performed by reverse phase high performance liquid chromatography [YMC-ODS, 4.6 mm$\phi$×250 mm;

gradient using eluant A=water-containing 0.1% TFA and eluant B=acetonitrile (0.1% TFA) (initial concentration of eluant B: 20%, gradient: 1%/min); flow rate: 1 ml/min]. After the fraction containing the product was freeze dried, 200 pl of water was added to give an aqueous solution containing the desired product (protein content: 19.1 μg/200 μl ).

Physical Property

Reverse phase high performance liquid chromatography
  Column: YMC-ODS AM303, 4.6 mmφ×250 mm (manufactured by Yamamura Chemical Co., Ltd.)
  Eluant: gradient
    eluant A: water (0.1% trifluoroacetic acid)
    eluant B: acetonitrile (0.1% trifluoroacetic acid)
  initial concentration of eluant B: 20%
  concentration gradient: 1%/min
  Flow rate: 1 ml/min
  Detection wavelength: 220 nm
  Retention time: 29.83 minutes
Amino acid analysis in the acid decomposition products (decomposition products after treating with 6 N hydrochloric acid-phenol at 110° C. for 24 hours)
  Glx 0.8 (1), Gly 1.1 (1), His 1.0 (1), Arg 0.8 (1), Met 0.3 (1), Phe* 1 (1), Trp—(1)
* standard amino acid; data within parentheses indicate calculated data; symbol—indicates data not measured.

EXAMPLE 23

PEG2-modified mouse D-NGF

To 850 pl of 50 mM sodium acetate buffer (pH 5.0) containing 350 μg of mouse β-NGF was added 0.5N NaOH to adjust pH to about 10. To the solution was added 25 mg of high purity PEG2 prepared in Example 1 at 4° C. The resulting mixture was then allowed to stand at 4° C. for 3.5 hours, during which the pH was kept at 9 to 10 with 0.1N NaOH. After neutralizing with 0.5N acetic acid, gel filtration was carried out using TSK G3000SW (7.5 mmφ×600 mm, 0.2M aqueous sodium chloride solution containing 5% ethanol) to give the fraction containing Product A and the fraction containing Product B. After the fractions were desalted and freeze dried, respectively, 200 μl each of water was added to give aqueous solutions containing Product A and Product B, respectively (protein content: Product A, 0.73 pg/μl; Product B, 1 μg/μl). The thus obtained Product B was acted on PC12 cells in a concentration of 100 ng (protein)/ml; the number of cells with neurites was increased by about twice as compared to control.

Physical Property of Product A

High performance gel filtration chromatography
  Column: TSK-gel G3000SW 7.5 mmφ×600 mm (manufactured by TOSO Co., Ltd.)
  Eluant: 0.1M aqueous sodium chloride solution (containing 5% ethanol)
  Flow rate: 0.6 ml/min
  Detection wavelength: 220 nm
  Retention time: 18.74 minutes
Amino acid analysis in the acid decomposition products (decomposition products after treating with 6 N hydrochloric acid-phenol at 110° C. for 24 hours)
  Asx 9.7 (11), Glx 7.6 (8), Ser 9.5 (11) Gly 5.2 (5), His 4.0 (4), Arg 6.2 (7), Thr 11.8 (14), Ala* 8 (8), Pro 2.3 (2), Tyr 2.0 (2), Val 12.1 (13), Met 0.9 (1) Ile 5.0 (5), Leu 3.4 (3), Phe 6.9 (7), Lys 7.7 (8), Cys—(6), Trp—(3)
* standard amino acid; data within parentheses indicate calculated data; symbol—indicates data not measured.

Physical Property of Product B

High performance gel filtration chromatography
  Column: TSK-gel G3000SW 7.5 mmφ×600 nun (manufactured by TOSO Co., Ltd.)
  Eluant: 0.1M aqueous sodium chloride solution (containing 5% ethanol)
  Flow rate: 0.6 ml/min
  Detection wavelength: 220 nm
  Retention time: 20.41 minutes
Amino acid analysis in the acid decomposition products (decomposition products after treating with 6 N hydrochloric acid-phenol at 110° C. for 24 hours)
  Asx 9.3 (11), Glx 6.9 (8), Ser 9.5 (11) Gly 5.1 (5), His 4.2 (4), Arg 6.3 (7), Thr 12.0 (14), Ala* 8 (8), Pro 2.4 (2), Tyr 1.9 (2), Val 12.1 (13), Met 0.5 (1) Ile 4.9 (5), Leu 3.2 (3), Phe 6.8 (7), Lys 7.7 (8), Cys—(6), Trp—(3)
* standard amino acid; data within parentheses indicate calculated data; symbol—indicates data not measured.

EXAMPLE 24

PEG2-modified human ANP (1-28)

To 80 Hi of 0.1M borate buffer (pH 10) containing 0.54 mg of human ANP (1-28) was added 54 μl aqueous solution containing 7 mg of high purity PEG2 prepared in Example 1 at 4° C. The mixture was allowed to stand at 4° C. for 6.5 hours. After diluting with 1 ml of water, the mixture was neutralized with 2N acetic acid and then purified by reverse phase high performance liquid chromatography [YMC-ODS, 4.6 mmφ×250 mm; gradient using eluant A=water-containing 0.1% TFA and eluant B=acetonitrile (0.1% TFA) (initial concentration of eluant B: 25%, gradient: 1%/min); flow rate: 1 ml/min]. The fraction containing the product was freeze dried to give the desired product.

Physical Property

Reverse phase high performance liquid chromatography
  Column: YMC-ODS AM303, 4.6 mmφ×250 mm (manufactured by Yamamura Chemical Co., Ltd.)
  Eluant: gradient
    eluant A: water (0.1% trifluoroacetic acid)
    eluant B: acetonitrile (0.1% trifluoroacetic acid)
  initial concentration of eluant B: 25%
  concentration gradient: 1%/min
  Flow rate: 1 ml/min
  Detection wavelength: 220 nm
  Retention time: 22.77 minutes
Amino acid analysis in the acid decomposition products (decomposition products after treating with 6 N hydrochloric acid-phenol at 110° C. for 24 hours)
  Asx 1.9 (2), Glx 1.0 (1), Ser 4.8 (5), Gly 5.1 (5), Arg 5.2 (5), Ala 0.8 (1), Tyr 1.0 (1), Met 0.3 (1), Ile 1.1 (1), Leu* 2 (2), Phe 1.9 (2), Cys—(2)
* standard amino acid; data within parentheses indicate calculated data; symbol—indicates data not measured.

EXAMPLE 25

PEG2-modified swine elastase

In 540 μl of 0.1M borate buffer (pH 10) was dissolved 1.04 mg of swine elastase and, 6.90 mg of high purity PEG2 prepared in Example 1 was added to the solution at 4° C. The mixture was allowed to stand at 4° C. for 6.5 hours. After neutralizing with 0.1M acetic acid, purification was performed by gel filtration using TSK G3000PW$_{XL}$ [(7.8 mm$\phi$×300 mm)×2; 0.2M aqueous sodium chloride solution]. After the fraction containing the desired product was desalted and freeze dried, 100 $\mu$l of water was added to give an aqueous solution containing the product (protein content, 64.5 $\mu$g/100 $\mu$l).

The thus obtained modified product showed enzyme activity equivalent to the unmodified enzyme in a concentration of 2 $\mu$g (protein)/ml.

Physical Property

High performance gel filtration chromatography
    Column: TSK-gel G3000PW$_{XL}$ [(7.8 mm$\phi$×300 mm)×2 (manufactured by TOSO Co., Ltd.)]
    Eluant: 0.2M aqueous sodium chloride solution (containing 5% ethanol)
    Flow rate: 0.6 ml/min
    Detection wavelength: 220 nm
    Retention time: 20.89 minutes
Amino acid analysis in the acid decomposition products (decomposition products after treating with 6 N hydrochloric acid-phenol at 110° C. for 24 hours)
    Asx 21.8 (24), Glx 18.7 (19), Ser 20.8 (22), Gly 25.1 (25), His 6.2 (6), Arg 11.4 (12), Thr 16.7 (19), Ala* 17 (17), Pro 7.5 (7), Tyr 11.6 (11), Val 25.1 (27), Met 1.9 (2), Ile 9.6 (10), Leu 19.8 (18), Phe 3.2 (3), Lys 2.9 (3), Cys—(8), Trp—(7)
* standard amino acid; data within parentheses indicate calculated data; symbol—indicates data not measured.

EXAMPLE 26

PEG2-modified human interleukin-3

In 200 $\mu$l of 0.1M borate buffer (pH 10) was dissolved 50 $\mu$g of human interleukin-3 and, 8 mg of high purity PEG2 prepared in Example 1 was added to the solution at 4° C. The resulting mixture was allowed to stand at 4° C. for 24 hours. After neutralizing with 1N acetic acid, purification was performed by gel filtration using TSK G3000SW [7.5 mm$\phi$×600 mm, 0.1M aqueous sodium chloride solution (containing 5% ethanol)]. The fraction containing the desired product was desalted and concentrated to give 30 $\mu$l of an aqueous solution containing the product.

Physical Property

High performance gel filtration chromatography
    Column: TSK-gel G3000SW 7.5 mm$\phi$×600 mm (manufactured by TOSO Co., Ltd.)
    Eluant: 0.1M aqueous sodium chloride solution (containing 5% ethanol)
    Flow rate: 0.6 ml/min
    Detection wavelength: 220 nm
    Retention time: 17.67 minutes
Amino acid analysis in the acid decomposition products (decomposition products after treating with 6 N hydrochloric acid-phenol at 110° C. for 24 hours)
    Asx 19.5 (19), Glx 16.1 (14), Set 8.3 (7), Gly 2.8 (2), His 2.3 (3), Arg 5.8 (6), Thr 8.3 (11), Ala 11.6 (11), Pro 11.7 (9), Tyr 1.6 (1), Val 3.1 (2), Met 4.1 (3), Ile 8.5 (9), Leu* 20 (20), Phe 4.8 (5), Lys 9.1 (7), Cys—(2), Trp—(2)
* standard amino acid; data within parentheses indicate calculated data; symbol—indicates data not measured.

EXAMPLE 27

PEG2-modified bovine pancreatic trypsin inhibitor

In 350 $\mu$l of 0.07M borate buffer (pH 10) was dissolved 500 pg of bovine pancreatic trypsin inhibitor and, 15 mg of high purity PEG2 prepared in Example 1 was added to the solution at 4° C. The resulting mixture was allowed to stand at 4° C. for 44 hours. After neutralizing with 1N acetic acid, purification was performed by gel filtration using TSK G3000SW [7.5 mm$\phi$×600 mm, 0.1M aqueous sodium chloride solution (containing 5% ethanol)]. The fraction containing the desired product was desalted and concentrated to give 60 $\mu$l of an aqueous solution containing the product.

Physical Property

High performance gel filtration chromatography
    Column: TSK-gel G3000SW 7.5 mm$\phi$×600 mm (manufactured by TOSO Co., Ltd.)
    Eluant: 0.1M aqueous sodium chloride solution (containing 5% ethanol)
    Flow rate: 0.6 ml/min
    Detection wavelength: 220 nm
    Retention time: 18.44 minutes
Amino acid analysis in the acid decomposition products (decomposition products after treating with 6 N hydrochloric acid-phenol at 110° C. for 24 hours)
    Asx 4.8 (5), Glx 2.9 (3), Ser 1.0 (1), Gly 6.0 (6), Arg 4.5 (6), Thr 2.3 (3), Ala 6.2 (6), Pro 4.2 (4), Tyr 3.9 (4), Val 1.0 (1), Met 1.3 (1), Ile 1.4 (2), Leu* 2 (2), Phe 3.9 (4), Lys 3.0 (4), Cys—(6)
* standard amino acid; data within parentheses indicate calculated data; symbol—indicates data not measured.

EXAMPLE 28

PEG2-modified IAP

In 150 $\mu$l of 0.1M borate buffer (pH 10) was dissolved 150 $\mu$g of IAP and, 6 mg of high purity PEG2 prepared in Example 1 was added to the solution at 4° C. The resulting mixture was allowed to stand at 4° C. for 44 hours. After neutralizing with 1N acetic acid, purification was performed by gel filtration using TSK G3000SW [7.5 mm$\phi$×600 mm, 0.1M aqueous sodium chloride solution (containing 5% ethanol)]. The fraction containing the desired product was desalted to give 75 $\mu$l of an aqueous solution containing the product.

Physical Property

High performance gel filtration chromatography
    Column: TSK-gel G3000SW 7.5 mm$\phi$×600 mm (manufactured by TOSO Co., Ltd.)
    Eluant: 0.1M aqueous sodium chloride solution (containing 5% ethanol)
    Flow rate: 0.6 ml/min
    Detection wavelength: 220 nm
    Retention time: 15.9 minutes

EXAMPLE 29

PEG2-modified human somatostatin

In 400 pl of 0.1M borate buffer (pH 10) was dissolved 0.45 mg of human somatostatin and, 16.2 mg of high purity PEG2 prepared in Example 1 was added to the solution at 4° C. The mixture was allowed to stand at 4° C. for 26 hours. After neutralizing with 0.1M acetic acid, purification was performed by reverse phase high performance liquid chromatography [YMC-ODS, 4.6 mm$\phi$×250 mm; gradient using eluant A=water-containing 0.1% TFA and eluant B=acetonitrile (0.1% TFA) (initial concentration of eluant B: 25%, gradient: 1%/min); flow rate: 1 ml/min]. After the fraction containing the product was freeze dried, 75 $\mu$l of water was added to give an aqueous solution of the desired product (protein content: 0.70 $\mu$g/pl).

Physical Property

Reverse phase high performance liquid chromatography
  Column: YMC-ODS AM303, 4.6 mm$\phi$×250 mm (manufactured by Yamamura Chemical Co., Ltd.)
  Eluant: gradient
    eluant A: water (0.1% trifluoroacetic acid)
    eluant B: acetonitrile (0.1% trifluoroacetic acid)
  initial concentration of eluant B: 25%
  concentration gradient: 1%/min
  Flow rate: 1 ml/min
  Detection wavelength: 220 nm
  Retention time: 25.23 minutes
Amino acid analysis in the acid decomposition products (decomposition products after treating with 6 N hydrochloric acid-phenol at 110° C. for 24 hours)
  Asx 0.8 (1), Ser 0.9 (1), Gly 1.1 (1), Thr 1.6 (2), Ala* 1 (1), Phe 3.0 (3), Lys 1.8 (2), Cys—(2), Trp—(1)
* standard amino acid; data within parentheses indicate calculated data; symbol—indicates data not measured.

EXAMPLE 30

PEG2-modified SOD (PEG2-SOD)

SOD was dissolved in 0.1M borate buffer in 5 mg/ml and the solution was cooled to 4° C. PEG2 was added to the solution to react for 15 to 20 hours. The reaction solution was neutralized followed by removing an excess of PEG2 using a ultrafiltration apparatus for cutting a molecular weight of 30,000. Preparation examples are shown in Table 8.

TABLE 8
Conditions for Preparing PEG-2-SOD

| Lot No. | Source & Amount | PEG2 (mg) | Degree of Modification (%) | Activity (U/mg protein) |
|---|---|---|---|---|
| PEG2-SOD-1 | Human erythrocyte 5 mg | 134.8 | 58.43 | 378 (14.00%) |
| PEG2-SOD-2 | Bovine erythrocyte 25 mg | 337 | 33.75 | 599.0 (19.97%) |
| PEG2-SOD-3 | Bovine erythrocyte 25 mg | 678 | 62.84 | 437.0 (14.57%) |
| PEG2-SOD-4 | Bovine erythrocyte 25 mg | 1011 | 66.43 | 412.6 (13.75%) |
| PEG2-SOD-5 | E. coli 25 mg | 674 | 60.14 | 436.5 (14.55%) |
| PEG2-SOD-6 | E. coli 25 mg | 1011 | 64.50 | 390.3 (13.01%) |

Human erythrocyte SOD: 2700 U/mg protein
Bovine erythrocyte SOD: 3000 U/mg protein
E. coli SOD: 3000 U/mg protein
Activity: method by McCord, J.M. and Fidovich, I. [J. Biol. Chem., 244, 6049 (1969)]

TEST EXAMPLE 1

Reduction in antigenicity of PEG2-SOD-5 synthesized in Example 30 was examined.

Using Swiss-Webster strain female mice as one group, a solution of SOD or PEG2-SOD in 0.05M phosphate buffered saline having pH of 7.0 (hereafter abbreviated as PBS) was intraperitoneally (hereafter abbreviated as i.p.) administered in a dose of 0.1 mg protein once a week for consecutive 12 weeks. Blood was collected from the blood vessel behind the orbit on Weeks 0, 3, 6, 9 and 12 and stored at -20° C. Titer of each serum was determined by ELISA (enzyme-linked immunosorbent assay). The results are shown in Table 9.

TABLE 9
Immunological Activity of PEG2-SOD

| Sensitized Antigen | Challenged Antigen (1 μg protein) | Antigenicity (expressed by dilution magnification of antibody) |
|---|---|---|
| SOD (E. coli) | SOD (E. coli) | 1:150000 |
|  | PEG2-SOD-5 | 1:1050 |
| PEG2-SOD-5 | SOD | 1:710 |
|  | PEG2-SOD-5 | 1:150 |

EXAMPLE 31

PEG2-modified catalase (PEG2-catalase)

PEG2-modified catalase shown in Table 10 was synthesized in a manner similar to Example 30.

TABLE 10
Conditions for Preparing PEG-2-Catalase

| Lot No. | Source & Amount | PEG2 (mg) | Degree of modification (%) | Activity (U/mg protein) |
|---|---|---|---|---|
| PEG-2-catalase-1 | Bovine liver 25 mg | 340 | 37.2 | 592.2 (19.74%) |
| PEG-2-catalase-2 | Bovine liver 25 mg | 680 | 47.8 | 446.4 (14.88%) |
| PEG-2-catalase-3 | Bovine liver 25 mg | 1020 | 55.6 | 320.7 (10.69%) |
| PEG-2-catalase-4 | Aspergillus niger 25 mg | 350 | 35.2 | 1015 (20.30%) |
| PEG-2-catalase-5 | Aspergillus niger 25 mg | 700 | 47.0 | 668 (13.36%) |

Bovine liver catalase: 3000 U/mg protein
Aspergillus niger catalase: 5000 U/mg protein
Activity: one unit indicates an amount for decomposing 1.0 μmol of $H_2O_2$ at pH of 7.0 and 25° C. for one minute.

TEST EXAMPLE 2

Antigenicity of PEG2-modified catalase was examined in a manner similar to Test Example 1. The results are shown in Table 11.

TABLE 11
Immunological Activity of PEG2-Catalase

| Sensitized Antigen | Challenged Antigen (1 μg protein) | Antigenicity (expressed by dilution magnification of antibody) |
|---|---|---|
| Catalase (A. niger) | Catalase (A. niger) | 1:150000 |
|  | PEG2-catalase-5 | 1:880 |
| PEG2-catalase-5 | Catalase (A. niger) | 1:880 |
|  | PEG2-catalase-5 | 1:100 |

TEST EXAMPLE 3

Influence on mouse ischemic paw edema ($O_2^-$ producing test in the rear paw after ischemia and reperfusion)

ddY strain mouse of 8 week age was fixed on a fixing stand and the right rear paw was tied with suture thread to make one round. One end was fixed and 500 g of a weight was hung at the other end to cause ischemia for a definite period of time. In the test, a thickness of the paw was measured with slide calipers prior to and minutes after ischemia. Then, the paw was cut and its weight was also measured. Administered groups were control group (physiological saline was intravenously injected immediately before ischemia), group administered with SOD (bovine erythrocytes) and group administered with PEG2-SOD. SOD and PEG2-SOD were intravenously administered in doses of 10000 U/kg and 500 U/kg, respectively, at 30 minutes before ischemia and immediately before ischemia. Catalase and PEG2-catalase were also administered in a similar manner. Five (5) mice were used for one grouping. The effect was evaluated by [paw thickness (m m) of edema paw—paw thickness (m m) of control paw] of the substances as compared to that of control. The effect was also evaluated by [paw weight (mg) of edema paw—paw weight (mg) of control paw] of substances as compared to that of control. That is:

Effect A = suppression ratio A of isochemic paw edema =

$$100 - \frac{\text{substance (paw thickness of edema paw} - \text{paw thickness of control paw) mm}}{\text{control (paw thickness of edema paw} - \text{paw thickness of control paw) mm}} \times 100$$

When the value exceeds 40%, it is evaluated to be effective.

Effect B = suppression ratio B of isochemic paw edema =

$$100 - \frac{\text{substance (paw weight of edema paw} - \text{paw weight of control paw) mg}}{\text{control (paw weight of edema paw} - \text{paw weight of control paw) mg}} \times 100$$

When the value exceeds 60%, it is evaluated to be effective.

The results are shown in Table 12.

TABLE 12

Effect of SOD (bovine erythrocyte), PEG2-SOD-2, catalase (*A. niger*), PEG2-catalase-1 on $O_2^-$ producing test in mouse rear paw after ischemia and reperfusion

| Substance and Injection time | Effect A | Effect B |
|---|---|---|
| Control | 0 | 0 |
| SOD (10000 U/kg) 30 mins. before ischemia | 24 | 44 |
| SOD (10000 U/kg) immediately before ischemia | 50 | 64.6 |
| PEG2-SOD-2 (500 U/kg) 30 mins. before ischemia | 60 | 65 |
| PEG2-SOD-2 (500 U/kg) immediately before ischemia | 58 | 66 |
| Catalase (10000 U/kg) 30 mins. before ischemia | 18 | 38 |
| Catalase (10000 U/kg) immediately before ischemi | 48 | 60 |
| PEG2-catalase-1 (500 U/kg) 30 mins. before ischemia | 62 | 65 |
| PEG2-catalase-1 (500 U/kg) immediately before ischemia | 60 | 64 |

EXAMPLE 32

PEG2-modified human erythrocyte-derived Cu, Zn-SOD

After 2.5 ml of 0.1M borate buffer (pH 10.0) was added to 10.0 mg of human erythrocyte-derived Cu, Zn-SOD, 70.0 mg of high purity PEG2 prepared in Example 1 was added to the solution at 5° C. The resulting mixture was allowed to stand at 5° C. for 22 hours. Then pH of the mixture was adjusted to 6.8 with 2N aqueous acetic acid solution. The mixture was then desalted and concentrated by ultrafiltration. The concentrate was purified by passing through Sephacryl S-200 column (2.6 cm$\phi$×94 cm; 0.2M aqueous sodium chloride solution). The fraction containing the product was collected. After desalting and concentrating by ultrafiltration, 1.8 ml of an aqueous solution containing the desired product was obtained. The thus obtained modified product had an enzyme activity of 81% based on the unmodified SOD [cytochrome C method, J. Biol. Chem., 224., 6049 (1969)].

Physical Property

Reverse phase high performance liquid chromatography
Column: YMC-ODS AM303, 4.6 mm$\phi$×250 mm (manufactured by Yamamura Chemical Co., Ltd.)
Eluant: gradient
  eluant A: water (0.1% trifluoroacetic acid)
  eluant B: acetonitrile (0.1% trifluoroacetic acid)
initial concentration of eluant B: 30%
concentration gradient: 1%/min
Flow rate: 1 ml/min
Detection wavelength: 214 nm
Retention time: 16.66 minutes
High performance gel filtration chromatography
Column: TSK-gel G3000SW 7.5 mm$\phi$×600 nun (manufactured by TOSO Co., Ltd.)
Eluant: 0.2M aqueous sodium chloride solution (containing 5% ethanol)
Flow rate: 0.6 ml/min
Detection wavelength: 220 nm
Retention time: 18.27 minutes
Amino acid analysis in the acid decomposition products (decomposition products after treating with 6 N hydrochloric acid-phenol at 110° C. for 24 hours)
Asx 30.9 (36), Glx 24.1 (26), Ser 18.7 (20), Gly 47.1 (50), His 14.8 (16), Arg 8.4 (8), Thr 13.4 (16), Ala* 20.0 (20), Pro 11.1 (10), Val 24.2 (28), Ile 12.9 (18), Leu 19.7 (18), Phe 8.0 (8), Lys 19.4 (22)

* standard amino acid; data within parentheses indicate calculated data.
Degree of modification: 20% (trinitrobenzenesulfonic acid method)

EXAMPLE 33

PEG2-modified human erythrocyte-derived Cu, Zn-SOD

After 2.5 ml of 0.1M borate buffer (pH 10.0) was added to 5.20 mg of human erythrocyte-derived Cu, Zn-SOD, 185 mg of high purity PEG2 prepared in Example 1 was added to the solution at 5° C. The resulting mixture was allowed to stand at 5° C. for 24 hours. After completion of the reaction, pH of the mixture was adjusted to 6.7 with 2N aqueous acetic acid solution. The reaction solution was applied to Sephacryl S-200 column (2.6 cm$\phi$×94 cm; 0.2M aqueous sodium chloride solution) as it was to purify by gel filtration. The fraction containing the product was collected. After desalting and concentrating by ultrafiltration, 1.8 ml of an aqueous solution containing the desired product was obtained. The thus obtained modified product had an enzyme activity of 59% based on the unmodified SOD cytochrome C method].

Physical Property

Reverse phase high performance liquid chromatography

Column: YMC-ODS AM303, 4.6 mmφ×250 mm (manufactured by Yamamura Chemical Co., Ltd.)
Eluant: gradient
 eluant A: water (0.1% trifluoroacetic acid)
 eluant B: acetonitrile (0.1% trifluoroacetic acid)
initial concentration of eluant B: 30%
concentration gradient: 1%/min
Flow rate: 1 ml/min
Detection wavelength: 214 nm
Retention time: 18.42 minutes
High performance gel filtration chromatography:
 Column: TSK-gel G3000SW 7.5 mmφ×600 mm (manufactured by TOSO Co., Ltd.)
 Eluant: 0.2M aqueous sodium chloride solution (containing 5% ethanol)
 Flow rate: 0.6 ml/min
 Detection wavelength: 220 nm
 Retention time: 16.69 minutes
Amino acid analysis in the acid decomposition products (decomposition products after treating with 6 N hydrochloric acid-phenol at 110° C. for 24 hours)
 Asx 28.6 (36), Glx 21.8 (26), Ser 18.0 (20), Gly 45.0 (50), His 14.2 (16), Arg 7.9 (8), Thr 13.2 (16), Ala* 20.0 (20), Pro 10.8 (10), Val 23.4 (28), Ile 12.0 (18), Leu 18.5 (18), Phe 7.6 (8), Lys 17.8 (22)
* standard amino acid; data within parentheses indicate calculated data.
Degree of modification: 52% (trinitrobenzenesulfonic acid method)

EXAMPLE 34

PEG2-modified human erythrocyte-derived Cu, Zn-SOD

After 5.0 ml of 0.1M borate buffer (pH 10.0) was added to 5.20 mg of human erythrocyte-derived Cu, Zn-SOD, 740 mg of high purity PEG2 prepared in Example 1 was added to the solution at 5° C. The resulting mixture was allowed to stand at 5° C. for 14 hours. Furthermore, 740 mg of PEG2 was added to the mixture, which was allowed to stand at 5° C. for 5 hours. After completion of the reaction, 3 ml of water was added to the mixture and pH was adjusted to 6.8 with 2N aqueous acetic acid solution. The reaction solution was applied to Sephacryl S-200 column (2.6 cmφ×94 cm; 0.2M aqueous sodium chloride solution) as it was to purify by gel filtration. The fraction containing the product was collected. After desalting and concentrating by ultrafiltration, 1.8 ml of an aqueous solution containing the desired product was obtained. The thus obtained modified product had an enzyme activity of 36% based on the unmodified SOD [cytochrome C method].

Physical Property

High performance gel filtration chromatography
 Column: TSK-gel G3000SW 7.5 mmφ×600 nun (manufactured by TOSO Co., Ltd.)
 Eluant: 0.2M aqueous sodium chloride solution (containing 5% ethanol)
 Flow rate: 0.6 ml/min
 Detection wavelength: 220 nm
 Retention time: 15.91 minutes
High performance gel filtration chromatography
 Column: TSK-gel G3000PW 7.5 mmφ×600 mm (manufactured by TOSO Co., Ltd.)
 Eluant: 0.2M aqueous sodium chloride solution
 Flow rate: 0.6 ml/min
 Detection wavelength: 254 nm
 Retention time: 18.13 minutes Amino acid analysis in the acid decomposition products (decomposition products after treating with 6 N hydrochloric acid-phenol at 110° C. for 24 hours)
 Asx 26.4 (36), Glx 21.9 (26), Ser 17.2 (20), Gly 42.9 (50), His 13.6 (16), Arg 7.8 (8), Thr 12.5 (16), Ala* 20.0 (20), Pro 10.4 (10), Val 22.1 (28), Ile 11.5 (18), Leu 18.2 (18), Phe 7.3 (8), Lys 16.2 (22)
* standard amino acid; data within parentheses indicate calculated data.
Degree of modification: 77% (trinitrobenzenesulfonic acid method)

EXAMPLE 35

PEG2-modified bovine Cu, Zn-SOD

In 1.875 ml of 0.1M borate buffer (pH 10) was dissolved 7.5 mg of bovine Cu, Zn-SOD and, 240 mg of high purity PEG2 prepared in Example 1 was added to the solution at 4° C. The resulting mixture was allowed to stand at 4° C. for 2 hours. Then 3 ml of water was added to the mixture. After neutralizing with hydrochloric acid, gel filtration purification was performed using Sephacryl S-200 column (2.6 cmφ×80 cm; 0.2M aqueous sodium chloride solution). The fraction containing the product was subjected to ultrafiltration. After desalting and concentrating, 10 ml of an aqueous solution containing the desired product was obtained (protein content, 0.28 mg/ml).

Physical Property

High performance gel filtration chromatography
 Column: TSK-gel G3000SW 7.5 mmφ×600 mm (manufactured by TOSO Co., Ltd.)
 Eluant: 0.1M aqueous sodium chloride solution (containing 5% ethanol)
 Flow rate: 0.6 ml/min
 Detection wavelength: 220 nm
 Retention time: 17.03 minutes
Amino acid analysis in the acid decomposition products (decomposition products after treating with 6 N hydrochloric acid-phenol at 110° C. for 24 hours)
 Asx 14.8 (17), Glx 10.9 (11), Ser 6.9 (8), Gly 22.4 (25), His 6.5 (8), Arg 3.7 (4), Thr 10.0 (12), Ala* 9 (9), Pro 6.2 (6), Tyr 1.4 (1), Val 11.7 (15), Met 1.4 (1), Ile 6.5 (9), Leu 7.9 (8), Phe 3.9 (4), Lys 7.7 (10), Cys—(3)
* standard amino acid; data within parentheses indicate calculated data; symbol—indicates data not measured.

EXAMPLE 36

PEG2-modified bovine liver catalase

In 1.5 ml of 0.1M borate buffer (pH 10) was dissolved 5 mg of bovine liver catalase and, 90 mg of high purity PEG2 prepared in Example 1 was added to the solution at 4° C. The resulting mixture was allowed to stand at 4° C. for 24 hours. After neutralizing with 0.1 M acetic acid, the mixture was applied to Sephacryl S-200 column (2.6 cmφ×84 cm; 0.2M aqueous sodium chloride solution) to perform purification by gel filtration. The fraction containing the product was collected. After desalting and concentrating by ultrafiltration, the residue was freeze dried to give 4.7 mg of the desired product.

Physical Property

High performance gel filtration chromatography
 Column: TSK-gel G3000SW 7.5 mmφ×600 mm (manufactured by TOSO Co., Ltd.)
 Eluant: 0.1M aqueous sodium chloride solution+5% ethanol
 Flow rate: 0.6 ml/min
 Detection wavelength: 220 nm Retention time: 25.7 minutes

EXAMPLE 37

PEG2-modified uricase

In 2 ml of 0.1M borate buffer (pH 10.0) was dissolved 5 mg of uricase (candida) and, 100 mg of PEG2 was added to the solution to react them at 4° C. for 20 hours. The reaction solution was passed through a ultrafiltering membrane for cutting a molecular weight of 100,000 to remove unreacted PEG2. Thus, PEG2-modified uricase was obtained.

Degree of modification: 46.5%
Activity: 17.8% (when the activity of unmodified urikase was made 100)
Molecular weight: 433,000
Reactivity with antiserum against uricase: 1/1000 of unmodified uricase

EXAMPLE 38

PEG2-modified uricase

In 500 pl of 0.1M borate buffer (pH 10) was dissolved 1 mg of uricase (candida) and, 30 mg of high purity PEG2 prepared in Example 1 was added to the solution at 4° C. The resulting mixture was allowed to stand at 4° C. for 25 hours. After neutralizing with 0.1 M acetic acid, the mixture was applied to Sephacryl S-200 column (2.6 cm$\phi$ × 84 cm; 0.2M aqueous sodium chloride solution) to perform purification by gel filtration. The fraction containing the product was collected. After desalting and concentrating by ultrafiltration, 200 pl of an aqueous solution containing the desired product was obtained.

Physical Property

High performance gel filtration chromatography
  Column: TSK-gel G3000SW 7.5 mm$\phi$ × 600 mm (manufactured by TOSO Co., Ltd.)
  Eluant: 0.1M aqueous sodium chloride solution + 5% ethanol
  Flow rate: 0.6 ml/min
  Detection wavelength: 220 nm
  Retention time: 25.1 minutes

EXAMPLE 39

PEG2-modified bilirubin oxidase

In 0.5 ml of water was dissolved 5 mg of bilirubin oxidase (Myrothecium verrucaria). While maintaining its pH to 6.0, 30 mg of 1,6-hexyldiamine hydrochloride and 0.6 mg of water-soluble carbodiimide (1-ethyl-3-(dimethylaminopropyl)carbodiimide hydrochloride) were added to the solution to react them at 4° C. for 20 hours. After an excess of 1,6-hexyl-diamine and the water-soluble carbodiimide were removed by passing through a ultrafiltering membrane for cutting a molecular weight of 10,000, the resulting aqueous solution was freeze dried. In 0.5 ml of 0.1M borate buffer (pH 10.0) was dissolved 2.5 mg of the resulting aminobilirubin oxidase and, 12 mg of PEG2 was added to the solution to react them at 4° C. for 20 hours. The reaction solution was passed through a ultrafiltering membrane for cutting a molecular weight of 30,000 to remove unreacted PEG2. Thus, PEG2-modified bilirubin oxidase was obtained.

Molecular weight: 113,000
Activity: 27.8% (when the activity of unmodified bilirubin oxidase was made 100)
Half life: 300 minutes (the half life of unmodified bilirubin oxidase was 15 minutes)

EXAMPLE 40

PEG2-modified bovine serum albumin

In 0.1M borate buffer (pH 9.20) was dissolved 10 mg of serum albumin (bovine) and, 100 mg of PEG2 was added to the solution to react them at 4° C. for 20 hours. The reaction solution was passed through a ultrafiltering membrane for cutting a molecular weight of 50,000 to remove unreacted PEG2. Thus, the desired product was obtained.

Degree of modification: 42.0%
Reactivity with antiserum against bovine serum albumin: 1/1000 of unmodified bovine serum albumin

EXAMPLE 41

PEG2-modified urokinase

In 0.1M borate buffer (pH 10.0) was dissolved 10 mg of urokinase (human urine) and, 200 mg of PEG2 was added to the solution to react them at 4° C. for 20 hours. The reaction solution was treated with a ultrafiltering membrane for cutting a molecular weight of 30,000 to remove unreacted PEG2. Thus, the desired product was obtained.

Activity: 17.8% (when the activity of unmodified urokinase was made 100)

EXAMPLE 42

PEG2-modified hyaluronidase

In 20 ml of 0.1M borate buffer (pH 10.0) was dissolved 100 mg of hyaluronidase (bovine testes) and, 2 g of PEG2 was added to the solution to react them at 4° C. for 20 hours. The reaction solution was treated with a ultrafiltering membrane for cutting a molecular weight of 30,000 to remove unreacted PEG2. Thus, the desired product was obtained.

Degree of modification: 47.6%
Activity: 22.9% (when the activity of unmodified hyaluronidase was made 100)

EXAMPLE 43

PEG2-modified chondroitin ABC lyase

In 0.1M borate buffer (pH 10.0) was dissolved 1 mg of chondroitin ABC lyase (Proteus vulgaris) and, 20 mg of PEG2 was added to the solution to react them at 4° C. for 20 hours. The reaction solution was treated with a ultrafiltering membrane for cutting a molecular weight of 30,000 to remove unreacted PEG2. Thus, the desired product was obtained.

Molecular weight: 220,000
Activity: 21.4% (when the activity of unmodified chondroitin ABC lyase was made 100)

EXAMPLE 44

PEG2-modified house dust mite allergen (PEG2-HDMA)

In 3 ml of 0.1M borate buffer (pH 10.0) was dissolved 2 mg of protein containing purified extract of house dust mite as the main ingredient (molecular weight 17,000) and, 63.5 mg of PEG2 was added to the solution to react them at 4° C. for 20 hours. The reaction solution was diluted to 10-fold volumes with 0.015M phosphate buffer (pH 7.0). The unreacted PEG2 was removed using a ultrafiltering membrane for cutting a molecular weight of 30,000 to give PEG2-HDMA.

Degree of modification: 48.0% (trinitrobenzenesulfonic acid method)

Figure 7:
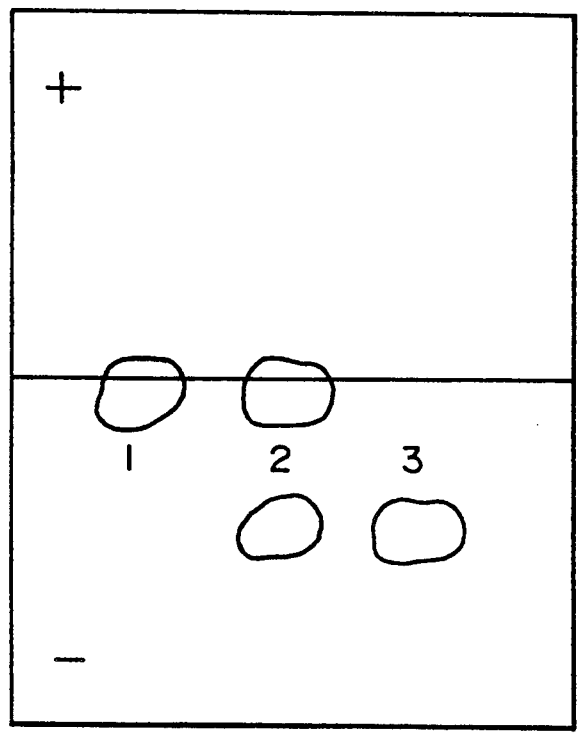
FIG. 7 shows electrophoretic pattern of PEG-HDMA obtained in Example 40.

Electrophoresis: Acetyl cellulose membrane 0.069M veronal buffer (pH 8.6), 0.5 mA/cm, Coomassie blue staining The results of the electrophoresis are shown in FIG. 7.

EXAMPLE 45
PEG2-modified human CRF

After 11.6 mg of high purity PEG2 prepared in Example 1 was added to 305 μl of 0.05M borate buffer (pH 10) containing 0.46 mg of human CRF at 4° C., the mixture was allowed to stand at 4° C. Further 7 hours after, 100 μl of 0.1M borate buffer (pH 10) was added to the mixture and, 5.8 mg each of PEG2 was added 23.5 hours after and 45.5 hours after, respectively. The mixture was allowed to stand at 4° C. for 72 hours in total. After neutralizing with 0.1M acetic acid, purification was performed by gel filtration using TSK G3000SW [7.5 mmφ×600 mm, 0.1M aqueous sodium chloride solution+5% ethanol; flow rate of 0.6 ml/min]. The fraction containing the desired product was collected and desalted and concentrated by ultrafiltration to give of an aqueous solution containing the product.

Physical Property

High performance gel filtration chromatography
  Column: TSK-gel G3000SW 7.5 mmφ×600 mm (manufactured by TOSO Co., Ltd.)
  Eluant: 0.1M aqueous sodium chloride solution+5% ethanol
  Flow rate: 0.6 ml/min
  Detection wavelength: 220 nm
  Retention time: 19.5 minutes Amino acid analysis in the acid decomposition products (decomposition products after treating with 6 N hydrochloric acid-phenol at 110° C. for 24 hours)
  Asx 2.3 (2), Glx 8.5 (9), Set 3.4 (3), His 2.2 (2), Arg 2.9 (3), Thr 1.3 (1), Ala* 4 (4), Pro 2.5 (2), Val 1.1 (1), Met 0.7 (2), Ile 1.9 (3), Leu 7.0 (7), Phe 1.2 (1), Lys 1.1 (1)

* standard amino acid; data within parentheses indicate calculated data.

EXAMPLE 46
PEG2-modified human IGF-I

After 5 mg of human IGF-I was dissolved in 2.5 ml of 0.1M borate buffer (pH 10), 50 mg of high purity PEG2 prepared in Example 1 was added to the solution at 4° C. over 4 hours by dividing PEG2 into 4 portions. After stirring at 4° C. for further an hour and half, 2 ml of water was added to the mixture. Then pH was adjusted to 7 with 1N aqueous hydrochloric acid solution. The reaction solution was applied to Sephacryl S-200 column (2.6 cmφ×93 cm; 0.2M aqueous sodium chloride solution) as it was to purify by gel filtration. The fraction containing the product was collected. After desalting and concentrating by ultrafiltration, 4.5 ml of an aqueous solution containing the desired product was obtained.

Physical Property

Reverse phase high performance liquid chromatography
  Column:μBONDASPHERE $C_{18}$ 3.9 mmφ×150 mm (manufactured by Waters Co., Ltd.)
  Eluant: gradient
    eluant A: water (0.1% trifluoroacetic acid)
    eluant B: acetonitrile (0.1% trifluoroacetic acid)
  initial concentration of eluant B: 30%
  concentration gradient: 1%/min
  Flow rate: 1 ml/min
  Detection wavelength: 220 nm
  Retention time: 23.2 minutes High performance gel filtration chromatography
  Column: TSK-gel G3000PW 7.5 mmφ×600 nun (manufactured by TOSO Co., Ltd.
  Eluant: 0.2M aqueous sodium chloride solution
  Flow rate: 0.6 ml/min
  Detection wavelength: 254 nm
  Retention time: 20.4 minutes Amino acid analysis in the acid decomposition products (decomposition products after treating with 6 N hydrochloric acid-phenol at 110° C. for 24 hours)
  Asx 4.5 (5), Glx 5.3 (6), Set 4.8 (5), Gly 7.7 (7), Arg 5.3 (6), Thr 2.8 (3), Ala 6.0 (6), Pro 4.9 (5), Tyr 2.9 (3), Val 2.6 (3), Met 0.4 (1), Ile 0.6 (1), Leu* 6 (6), Phe 4.2 (4), Lys 3.2 (3), Cys—(6)

* standard amino acid; data within parentheses indicate calculated data; symbol—indicates data not measured.

EXAMPLE 47
PEG2-modified human IGF-I

In 500 pl of 0.1M borate buffer (pH 10) was dissolved 5.0 mg of human IGF-I and, 13.4 mg of high purity PEG2 prepared in Example 1 was added to the solution at 4° C. The mixture was allowed to stand at 4° C. for 22 hours. After neutralizing with 0.1M acetic acid, purification was performed by passing through Sephacryl S-200 column (2.6 cmφ×94 cm; 0.2M aqueous sodium chloride solution). The fractions containing Product A and Product-B were desalted and concentrated by ultrafiltration, respectively to 250 μl each of aqueous solutions containing Product A and Product B (protein content: Product A, 753 μg/250 μl; Product B, 341 μg/250 μl).

The thus obtained product B exhibited growth promoting activity on growth of cartilage by about 1/100 of the unmodified human IGF-I, in the determination of growth promoting activity using weight increment of cartilage tissue in organ culture of chick embryonic femur (cartilage).

Physical Property of Product A

High performance gel filtration chromatography
  Column: TSK-gel G3000SW 7.5 mmφ×600 mm (manufactured by TOSO Co., Ltd.)
  Eluant: 0.1M aqueous sodium chloride solution (containing 5% ethanol)
  Flow rate: 0.6 ml/min
  Detection wavelength: 220 nm
  Retention time: 20.76 minutes Amino acid analysis in the acid decomposition products (decomposition products after treating with 6 N hydrochloric acid-phenol at 110° C. for 24 hours)
  Asx 4.6 (5), Glx 5.3 (6), Ser 4.9 (5), Gly 7.3 (7), Arg 6.3 (6), Thr 2.8 (3), Ala 6.2 (6), Pro 5.2 (5), Tyr 3.1 (3), Val 2.4 (3), Met 0.5 (1), Ile 0.6 (1), Leu* 6 (6), Phe 3.9 (4), Lys 2.9 (3), Cys—(6)

* standard amino acid; data within parentheses indicate calculated data; symbol—indicates data not measured.

Physical Property of Product B

High performance gel filtration chromatography

Column: TSK-gel G3000SW 7.5 mmφ×600 nun (manufactured by TOSO Co., Ltd.)
Eluant: 0.1M aqueous sodium chloride solution (containing 5% ethanol)
Flow rate: 0.6 ml/min
Detection wavelength: 220 nm
Retention time: 21.15 minutes Amino acid analysis in the acid decomposition products (decomposition products after treating with 6 N hydrochloric acid-phenol at 110° C. for 24 hours)
Asx 5.1 (5), Glx 6.0 (6), Ser 4.9 (5), Gly 7.3 (7), Arg 6.3 (6), Thr 2.7 (3), Ala 6.3 (6), Pro 5.5 (5), Tyr 3.0 (3), Val 2.6 (3), Met 1.2 (1), Ile 0.8 (1), Leu* 6 (6), Phe 3.8 (4), Lys 3.2 (3), Cys—(6)

* standard amino acid; data within parentheses indicate calculated data; symbol—indicates data not measured.

EXAMPLE 48

PEG2-modified human IGF-II

In 84 pl of 0.1M borate buffer (pH 10) was dissolved 200 pg of human IGF-II and, 16 μl of an aqueous solution containing 2 mg of high purity PEG2 prepared in Example 1 was added to the solution. The mixture was allowed to stand at 4° C. for 16 hours. After 16 of an aqueous solution containing 2 mg of PEG2 was further added thereto, the mixture was allowed to stand at 4° C. for 20 hours. After neutralizing with 1N acetic acid, purification was performed by gel filtration using TSK G3000SW [7.5 mmφ×600 mm, 0.2M aqueous sodium chloride solution (5% ethanol)]. After the fraction containing the desired product was desalted and freeze dried, 80 μl of water was added to give an aqueous solution containing the product (protein content, 73 μg/80 μl).

Physical Property

High performance gel filtration chromatography
Column: TSK-gel G3000 SW 7.5 mmφ×600 mm (manufactured by TOSO Co., Ltd.)
Eluant: 0.2M aqueous sodium chloride solution (containing 5% ethanol)
Flow rate: 0.6 ml/min
Detection wavelength: 220 nm
Retention time: 19.51 minutes Amino acid analysis in the acid decomposition products (decomposition products after treating with 6 N hydrochloric acid-phenol at 110° C. for 24 hours)
Asx 2.7 (3), Glx 6.6 (7), Ser 6.7 (7), Gly 5.2 (5), Arg 6.7 (8), Thr 3.3 (4), Ala* 5 (5), Pro 2.9 (3), Tyr 2.8 (3), Val 3.3 (4), Ile 0.6 (1), Leu 5.4 (6), Phe 4.0 (4), Lys 1.1 (1), Cys—(6)

* standard amino acid; data within parentheses indicate calculated data; symbol—indicates data not measured.

EXAMPLE 49

PEG2-modified human GH

After 0.9 mg of high purity PEG2 prepared in Example 1 was added to 15 μl of 0.05M borate buffer (pH containing 25 μg of human GH, the mixture was allowed to stand at 3° C. for 22 hours. Then, purification was performed by gel filtration using TSK G3000SW [7.5 mmφ×600 mm, 0.1M aqueous sodium chloride solution (containing 5% ethanol)]. The fraction containing the desired product was desalted and concentrated to give 100 μl of an aqueous solution containing the product (protein content, 7 μg/100 μl).

Physical Property

High performance gel filtration chromatography
Column: TSK-gel G3000SW 7.5 mmφ×600 mm (manufactured by TOSO Co., Ltd.)
Eluant: 0.1M aqueous sodium chloride solution (containing 5% ethanol)
Flow rate: 0.6 ml/min
Detection wavelength: 220 nm
Retention time: 16.3 minutes Amino acid analysis in the acid decomposition products (decomposition products after treating with 6 N hydrochloric acid-phenol at 110° C. for 24 hours)
Asx 18.0 (20), Glx 26.9 (27), Ser 17.1 (18), Gly 13.5 (8), His 3.1 (3), Arg 8.6 (11), Thr 8.4 (10), Ala* 7 (7), Pro 7.6 (8), Tyr 7.9 (8), Val 6.7 (7), Met 2.6 (3), Ile 7.4 (8), Leu 25.5 (26), Phe 12.5 (13), Lys 8.2 (9), Cys—(4), Trp—(1)

* standard amino acid; data within parentheses indicate calculated data; symbol—indicates data not measured.

EXAMPLE 50

PEG2-modified human t-PA

After 9.6 ml of 0.1M borate buffer (pH 9.5; containing 1M potassium thiocyanate) was added to 340 of a solution containing human t-PA (29.3 mg of t-PA/ml, pH 3), 164.2 mg of high purity PEG2 prepared in Example 1 was added to the solution at 4° C. The resulting mixture was allowed to stand at 4° C. for 19 hours. After completion of the reaction, pH of the mixture was adjusted to 3 with 1N aqueous hydrochloric acid solution. After centrifugation, the resulting supernatant was applied to Sephacryl S-200 column (2.6 cmφ×84 cm; 0.2M aqueous sodium chloride solution, pH 3) as it was to purify by gel filtration. The fraction containing the product was collected. After desalting and concentrating by ultrafiltration, 100 μl of an aqueous solution containing the desired product was obtained (protein content, 3.53 mg/ml).

With respect to the thus obtained modified product, its amidolytic activity was determined using S-(Ile-Pro-Arg-pNA) as substrate. The activity showed $4.0 \times 10^5$ IU/ml.

Physical Property

Reverse phase high performance liquid chromatography
Column: YMC-ODS AM303, 4.6 mmφ×250 mm (manufactured by Yamamura Chemical Co., Ltd.)
Eluant: gradient
eluant A: water (0.1% trifluoroacetic acid)
eluant B: acetonitrile (0.1% trifluoroacetic acid)
initial concentration of eluant B: 20%
concentration gradient: 1%/min
Flow rate: 1 ml/min
Detection wavelength: 214 nm
Retention time: 26.0 minutes High performance gel filtration chromatography:
Column: TSK-gel G3000PW 7.5 mmφ×600 mm (manufactured by TOSO Co., Ltd.)
Eluant: 0.2M aqueous sodium chloride solution
Flow rate: 0.6 ml/min
Detection wavelength: 254 nm
Retention time: 20.8 minutes Amino acid analysis in the acid decomposition products (decomposition products after treating with 6 N hydrochloric acid-phenol at 110° C. for 24 hours)

Asx 53.0 (50), Glx 53.4 (52), Ser 46.5 (48), Gly 45.3 (43), His 16.9 (16), Arg 31.5 (35), Thr 23.4 (25), Ala* 32 (32), Pro 27.4 (29), Tyr 23.2 (24), Val 22.4 (25), Met 7.5 (5), Ile 16.3 (19), Leu 36.9 (39), Phe 14.9 (19), Lys 17.8 (16), Cys—(35), Trp—(13)

* standard amino acid; data within parentheses indicate calculated data; symbol—indicates data not measured.

EXAMPLE 51

PEG2-modified ubiquitin

After 6 mg of ubiquitin (human) was dissolved in 3 ml of 0.1M borate buffer (pH 10), 520 mg of high purity PEG2 prepared in Example 1 was added to the solution at 4° C. over an hour and half by dividing PEG2 into 3 portions. After stirring at 4° C. for further 2 hours, 2 ml of water was added to the mixture. Then pH was adjusted to 7 with 1N aqueous hydrochloric acid solution. The reaction solution was applied to Sephacryl S-200 column (2.6 cm$\phi \times$93 cm; 0.2M aqueous sodium chloride solution) as it was to purify by gel filtration. The fraction containing the product was collected. After desalting and concentrating by ultrafiltration, 4.5 ml of an aqueous solution containing the desired product was obtained.

Physical Property

Reverse phase high performance liquid chromatography
  Column: $\mu$BONDASPHERE C$_4$
    3.9 mm$\phi \times$150 mm (manufactured by Waters Co., Ltd.)
  Eluant: gradient
    eluant A: water (0.1% trifluoroacetic acid)
    eluant B: acetonitrile (0.1% trifluoroacetic acid)
  initial concentration of eluant B: 25%
  concentration gradient: 1%/min
  Flow rate: 1 ml/min
  Detection wavelength: 220 nm
  Retention time: 23.5 minutes
High performance gel filtration chromatography:
  Column: TSK-gel G3000PW Co., Ltd. 7.5 mm$\phi \times$600 mm (manufactured by TOSO Co., Ltd.
  Eluant: 0.2M aqueous sodium chloride solution
  Flow rate: 0.6 ml/min
  Detection wavelength: 254 nm
  Retention time: 20.3 minutes
Amino acid analysis in the acid decomposition products (decomposition products after treating with 6 N hydrochloric acid-phenol at 110° C. for 24 hours)
  Asx 6.9 (7), Glx 12.3 (12), Set 3.1 (3) Gly 7.2 (4), His 1.1 (1), Arg 3.8 (4), Thr 6.8 (7), Ala 3.2 (3), Pro 3.6 (3), Tyr 1.1 (1), Val 4.3 (4), Met 0.6 (1), Ile 6.6 (7), Leu* 9 (9), Phe 1.7 (2), Lys 5.0 (7)

* standard amino acid; data within parentheses indicate calculated data.

EXAMPLE 52

PEG2-modified mouse GM-CSF

After 500 $\mu$l of 0.1M borate buffer (pH 10) containing 36 mg of high purity PEG2 prepared in Example 1 was added to 500 $\mu$l of an aqueous solution containing 500 $\mu$g of mouse GM-CSF, the mixture was allowed to stand at room temperature for 2.5 hours. Purification was performed using reverse phase high performance liquid chromatography [$\mu$BONDASPHERE C$_{18}$, 3.9 mm$\phi \times$15 cm; gradient using eluant A=water-containing 0.1% TFA and eluant B: acetonitrile (0.1% trifluoroacetic acid) (initial concentration of eluant B: 0%; 30% 15 minutes after and 90% 75 minutes after); flow rate: 1 ml/min]. The fraction containing the product was again purified by reverse phase high performance liquid chromatography [$\mu$BONDASPHERE C$_{18}$, 3.9 mm$\phi \times$15 cm; gradient using eluant A=water-containing 0.1% TFA and eluant B=acetonitrile (0.1% trifluoro-acetic acid) (initial concentration of eluant B, 36%; gradient, 1%/min); flow rate: 1 ml/min]. After freeze drying the fraction containing the desired product, 200 $\mu$l of water was added to give an aqueous solution containing the desired product (protein content, 85 $\mu$g/200 $\mu$l ) .

The resulting modified product showed an activity of $8 \times 10^7$ U/mg in the $^3$H-thymidine incorporation assay into mouse bone marrow cells. Furthermore, intraperitoneal administration of the modified product to C3H/He mice resulted in being removed from plasma with the half life of about 7 hours (about 40 minutes with mouse GM-CSF).

Physical Property

Reverse phase high performance liquid chromatography
  Column: $\mu$BONDASPHERE C$_{18}$ 3.9 mm$\phi \times$150 mm (manufactured by waters Co., Ltd.)
  Eluant: gradient
    eluant A: water (0.1% trifluoroacetic acid)
    eluant B: acetonitrile (0.1% trifluoroacetic acid)
  initial concentration of eluant B: 36%
  concentration gradient: 1%/min
  Flow rate: 1 ml/min
  Detection wavelength: 220 nm
  Retention time: 13.63 minutes
Amino acid analysis in the acid decomposition products (decomposition products after treating with 6 N hydrochloric acid-phenol at 110° C. for 24 hours)
  Asx 9.8 (11), Glx 13.0 (15), Ser 3.8 (5), Gly 3.0 (3), His 0.7 (1), Arg 3.5 (4), Thr 13.6 (16), Ala* 6 (6), Pro 8.5 (9), Tyr 3.5 (4), Val 8.1 (9), Met 1.0 (3), Ile 4.5 (5), Leu 10.5 (11), Phe 6.2 (7), Lys 10.0 (11), Cys—(4), Trp—(1)

* standard amino acid; data within parentheses indicate calculated data; symbol—indicates data not measured.

EXAMPLE 53

PEG2-modified peptide T

In 500 $\mu$l of 0.1M borate buffer (pH 10) was dissolved 0.56 mg of peptide T and, 19.6 mg of high purity PEG2 prepared in Example 1 was added to the solution. The resulting mixture was allowed to stand at 4° C. for 25 hours. After neutralizing with 0.1M acetic acid, purification was performed by reverse phase high performance liquid chromatography [YMC-ODS, 4.6 mm$\phi \times$250 mm; gradient using eluant A=water-containing 0.1% TFA and eluant B=acetonitrile (0.1% TFA) (initial concentration of eluant B: 25%, gradient: 1%/min); flow rate: 1 ml/min]. After the fraction containing the product was freeze dried, 200 $\mu$l of water was added to give an aqueous solution containing the desired product.

Physical Property

Reverse phase high performance liquid chromatography
  Column: YMC-ODS AM303, 4.6 mm$\phi \times$250 mm (manufactured by Yamamura Chemical Co., Ltd.)
  Eluant: gradient
    eluant A: water (0.1% trifluoroacetic acid)
    eluant B: acetonitrile (0.1% trifluoroacetic acid)

initial concentration of eluant B: 25%
concentration gradient: 1%/min
Flow rate: 1 ml/min
Detection wavelength: 220 nm
Retention time: 25.1 minutes Amino acid analysis in the acid decomposition products (decomposition products after treating with 6 N hydrochloric acid-phenol at 110° C. for 24 hours)
Asx 0.9 (1), Ser 0.9 (1), Thr 3.1 (4), Ala* 1 (1), Tyr 1.0 (1)

* standard amino acid; data within parentheses indicate calculated data.

EXAMPLE 54

PEG2-modified STF

In 500 μl of 0.1M borate buffer (pH 10) was dissolved 0.58 mg of STF and, 20.3 mg of high purity PEG2 prepared in Example 1 was added to the solution. The resulting mixture was allowed to stand at 4° C. for 25 hours. After neutralizing with 0.1M acetic acid, purification was performed by reverse phase high performance liquid chromatography [YMC-ODS, 4.6 mmφ×250 mm; gradient using eluant A=water-containing 0.1% TFA and eluant B=acetonitrile (0.1% TFA) (initial concentration of eluant B: 25%, gradient: 1%/min); flow rate: 1 ml/min]. After the fraction containing the product was freeze dried, 200 μl of water was added to give an aqueous solution containing the desired product.

Physical Property

Reverse phase high performance liquid chromatography
Column: YMC-ODS AM303, 4.6 mmφ×250 mm (manufactured by Yamamura Chemical Co., Ltd.)
Eluant: gradient
  eluant A: water (0.1% trifluoroacetic acid)
  eluant B: acetonitrile (0.1% trifluoroacetic acid)
initial concentration of eluant B: 25%
concentration gradient: 1%/min
Flow rate: 1 ml/min
Detection wavelength: 220 nm
Retention time: 24.4 minutes Amino acid analysis in the acid decomposition products (decomposition products after treating with 6 N hydrochloric acid-phenol at 110° C. for 24 hours)
Asx 0.8 (1), Glx 1.6 (2), Ser 1.8 (2), Gly 2.0 (2), Ala* 1 (1), Lys 1.0 (1)

* standard amino acid; data within parentheses indicate calculated data.

EXAMPLE 55

PEG2-modified human ACTH (1-24)

After 48.0 mg of high purity PEG2 prepared in Example 1 was added to 305 μl of 0.05M borate buffer (pH 10) containing 0.47 mg of human ACTH (1-24) at 4° C., the mixture was allowed to stand at 4° C. Further 7 hours after, 100 μl of 0.1M borate buffer (pH 10) was added to the mixture and, 24.0 mg each of PEG2 was added 27 hours after and 45.5 hours after, respectively. The mixture was allowed to stand at 4° C. for 72 hours in total. After neutralizing with 0.1M acetic acid, purification was performed by gel filtration using TSK G3000SW [7.5 mmφ×600 mm, 0.1M aqueous sodium chloride solution+5% ethanol; flow rate of 0.6 ml/min]. The fraction containing the desired product was collected and desalted and concentrated by ultrafiltration to give 200 μl of an aqueous solution containing the product.

Physical Property

High performance gel filtration chromatography
Column: TSK-gel G3000SW 7.5 mmφ×600 mm (manufactured by TOSO Co., Ltd.)
Eluant: 0.1M aqueous sodium chloride solution+5% ethanol
Flow rate: 0.6 ml/min
Detection wavelength: 220 nm
Retention time: 17.4 minutes Amino acid analysis in the acid decomposition products (decomposition products after treating with 6 N hydrochloric acid-phenol at 110° C. for 24 hours)
Glx 0.8 (1), Ser 1.9 (2), Gly 2.1 (2), His 1.0 (1), Arg 2.9 (3), Pro 2.9 (3), Tyr 1.4 (2), Val 3.2 (3), Met 0.4 (1), Phe* 1 (1), Lys 3.1 (4), Trp—(1)

* standard amino acid; data within parentheses indicate calculated ones; symbol—indicates data not measured.

EXAMPLE 56

PEG2-modified human PTH (1-34)

After 28.4 mg of high purity PEG2 prepared in Example 1 was added to 305 μl of 0.05M borate buffer (pH 10) containing 0.49 mg of human PTH (1-34) at 4° C., the mixture was allowed to stand at 4° C. Further 7 hours after, 100 μl of 0.1M borate buffer (pH 10) was added to the mixture and, 14.2 mg each of PEG2 was added 23.5 hours after and 45.5 hours after, respectively. The mixture was allowed to stand at 4° C. for 72 hours in total. After neutralizing with 0.1M acetic acid, purification was performed by gel filtration using TSK G3000SW [7.5 mmφ×600 mm, 0.1M aqueous sodium chloride solution+5% ethanol; flow rate of 0.6 ml/min]. The fraction containing the desired product was collected and desalted and concentrated by ultrafiltration to give of an aqueous solution containing the product.

Physical Property

High performance gel filtration chromatography
Column: TSK-gel G3000SW 7.5 mmφ×600 mm (manufactured by TOSO Co., Ltd.)
Eluant: 0.1M aqueous sodium chloride solution+5% ethanol
Flow rate: 0.6 ml/min
Detection wavelength: 220 nm
Retention time: 19.2 minutes Amino acid analysis in the acid decomposition products (decomposition products after treating with 6 N hydrochloric acid-phenol at 110° C. for 24 hours)
Asx 3.9 (4), Glx 4.8 (5), Ser 2.8 (3), Gly 1.3 (1), His 2.8 (3), Arg 2.0 (2), Val 3.1 (3), Met 1.4 (2), Ile 1.0 (1), Leu* 5 (5), Phe 1.0 (1), Lys 2.4 (3), Trp—(1)

* standard amino acid; data within parentheses indicate calculated ones; symbol—indicates data not measured.

EXAMPLE 57

PEG2-modified human glucagon

After 17.7 mg of high purity PEG2 prepared in Example 1 was added to 305 μl of 0.05M borate buffer (pH 10) containing 0.51 mg of glucagon (human) at 4° C., the mixture was allowed to stand at 4° C. Further 7 hours after, 100 μl of 0.1M borate buffer (pH 10) was added to the mixture and, 8.9 mg each of PEG2 was added 23.5 hours after and 45.5 hours after, respectively. The mixture was allowed to stand at 4° C. for 72 hours in total. After neutralizing with 0.1M acetic acid, purification was performed by gel filtration using TSK G3000SW [7.5 mmφ×600 mm, 0.1M aqueous sodium chloride solution+5% ethanol; flow rate of 0.6 ml/min]. The fraction containing the desired product was collected and desalted and concentrated by ultrafiltration to give 200 μl of an aqueous solution containing the product.

Physical Property

High performance gel filtration chromatography
  Column: TSK-gel G3000SW 7.5 mmφ×600 nun (manufactured by TOSO Co., Ltd.)
  Eluant: 0.1M aqueous sodium chloride solution+5% ethanol
  Flow rate: 0.6 ml/min
  Detection wavelength: 220 nm
  Retention time: 19.8 minutes
Amino acid analysis in the acid decomposition products (decomposition products after treating with 6 N hydrochloric acid-phenol at 110° C. for 24 hours)
  Asx 3.5 (4), Glx 2.4 (3), Ser 3.8 (4), Gly 1.2 (1), His 0.8 (1), Arg 1.9 (2), Thr 2.8 (3), Ala 1.3 (1), Tyr 2.1 (2), Val 1.1 (1), Met 0.5 (1), Leu* 2 (2), Phe 2.0 (2), Lys 0.8 (1), Trp—(1)

* standard amino acid; data within parentheses indicate calculated ones; symbol—indicates data not measured.

EXAMPLE 58

PEG2-modified human CCK-octapeptide (26-33)

After 24.2 mg of high purity PEG2 prepared in Example 1 was added to 305 pl of 0.05M borate buffer (pH 10) containing 0.46 mg of human CCK-octapeptide (26-33) (Sulfated Form) at 4° C., the mixture was allowed to stand at 4° C. Further 7 hours after, 100 μl of 0.1M borate buffer (pH 10) was added to the mixture and, 12.1 mg each of PEG2 was added 23.5 hours after and 45.5 hours after, respectively. The mixture was allowed to stand at 4° C. for 72 hours in total. After neutralizing with 0.1M acetic acid, purification was performed by reverse phase high performance liquid chromatography YMC-ODS, 4.6 mmφ×250 mm; gradient using eluant A=water-containing 0.1% TFA and eluant B=acetonitrile (0.1% TFA) (initial concentration of eluant B: 25%, gradient: 1%/min); flow rate: 1 ml/min]. After the fraction containing the product was freeze dried, 200 μl of water was added to give an aqueous solution containing the desired product.

Physical Property

Reverse phase high performance liquid chromatography
  Column: YMC-ODS AM303, 4.6 mmφ×250 mm (manufactured by Yamamura Chemical Co., Ltd.)
  Eluant: gradient
    eluant A: water (0.1% trifluoroacetic acid)
    eluant B: acetonitrile (0.1% trifluoroacetic acid)
    initial concentration of eluant B: 25%
    concentration gradient: 1%/min
  Flow rate: 1 ml/min
  Detection wavelength: 220 nm
  Retention time: 26.7 minutes
Amino acid analysis in the acid decomposition products (decomposition products after treating with 6 N hydrochloric acid-phenol at 110° C. for 24 hours)
  Asx 2.1 (2), Gly 1.1 (1), Tyr 1.1 (1), Met 1.0 (2), Phe* 1 (1), Trp—(1)

* standard amino acid; data within parentheses indicate calculated ones; symbol—indicates data not measured.

EXAMPLE 59

PEG2-modified α-globulin

In 20 ml of 0.1M borate buffer (pH 10.0) was dissolved 100 mg of α-globulin fraction IV (swine) and, 200 mg of PEG2 was added to the solution to react them at 4° C. for 20 hours. The reaction solution was treated with a ultrafiltering membrane for cutting a molecular weight of 30,000 to remove unreacted PEG2. Thus, the desired product was obtained.
Degree of modification: 44.7%

EXAMPLE 60

PEG2-modified γ-globulin

In 20 ml of 0.1M borate buffer (pH 10.0) was dissolved 100 mg of γ-globulin fraction II (swine) and, 2000 mg of PEG2 was added to the solution to react them at 4° C. for 20 hours. The reaction solution was treated with a ultrafiltering membrane for cutting a molecular weight of 30,000 to remove unreacted PEG2. Thus, the desired product was obtained.
Degree of modification: 38.9%

EXAMPLE 61

PEG2-modified transferrin

In 1 ml of 0.1M borate buffer (pH 10.0) was dissolved 5 mg of transferrin, partially Iron-saturated (mouse) and, 100 mg of PEG2 was added to the solution to react them at 4° C. for 20 hours. The reaction solution was treated with a ultrafiltering membrane for cutting a molecular weight of 100,000 to remove unreacted PEG2. Thus, the desired product was obtained.
Degree of modification: 33.9%

EXAMPLE 62

PEG2-modified lipoprotein

To 10 ml (about 100 mg) of lipoprotein cholesterol solution (lipoprotein, 50%) was added 10 ml of 0.1M borate buffer (pH 10.0) and, 2 g of PEG2 was further added to the mixture to react them at 4° C. for 20 hours. The reaction solution was treated with a ultrafiltering membrane for cutting a molecular weight of 30,000 to remove unreacted PEG2.
Degree of modification: 21.4%

EXAMPLE 63

PEG2-modified endotoxin

In 20 ml of 0.1M borate buffer (pH 10.0) was dissolved 10 mg of endotoxin (*E. coli* 0111:B) and, 200 mg of PEG2 was added to the solution to react them at 4° C. for 20 hours. The reaction solution was treated with a ultrafiltering membrane for cutting a molecular weight of 300,000 to remove unreacted PEG2.
Degree of modification of ethanolamine group: 38.7%
Endotoxin activity (with reagent of Limulus test in colorimetry): 1/100 of endotoxin (*E. coli* 0111:B)

EXAMPLE 64

PEG2-modified elastase

In 20 ml of water was dissolved 100 mg of elastase (swine) and 2 g of PEG2 was added to the solution. While gradually increasing pH with 0.1N sodium hydroxide at 4° C. finally to 10.0, the mixture was reacted at 4° C. for 20 hours. The reaction solution was treated with a ultrafiltering membrane for cutting a molecular weight of 30,000 to remove unreacted PEG2.
Degree of modification: 39.9%
Activity: 27.8% (when the activity of unmodified elastase was made 100)

EXAMPLE 65

PEG2-modified human t-PA

After 547 μl of 0.1M borate buffer (pH 10; containing 1M potassium thiocyanate) was added to 171 μl of a solution containing human t-PA (29.3 mg of t-PA/ml, pH 3), 16.4 mg of high purity PEG2 prepared in Example 1 was added to the solution at 4° C. The resulting mixture was allowed to stand at 4° C. for 24 hours. After completion of the reaction, the mixture was neutralized with 0.1M acetic acid. After centrifugation, the resulting supernatant was applied to Sephacryl S-200 column (2.6 cm$\phi$×84 cm; 0.2M aqueous sodium chloride solution) as it was to purify by gel filtration. The fractions containing Product A and Product B were collected, respectively. After desalting and concentrating by ultrafiltration, 150 μl of an aqueous solution containing Product A (protein content, 5.63 mg/ml) and 200 μl of an aqueous solution containing Product B (protein content, 3.46 mg/ml) were obtained.

With respect to the thus obtained modified products, their amidolytic activity was determined using S-2288 (Ile-Pro-Arg-pNA) as substrate. Product A had the activity of $1.2 \times 10^6$ IU/ml and Product B showed the activity of $9.3 \times 10^5$ IU/ml.

Physical Property of Product A

High performance gel filtration chromatography
  Column: TSK-gel G3000PW 7.5 mm$\phi$×600 nun (manufactured by TOSO Co., Ltd.)
  Eluant: 0.2M aqueous sodium chloride solution
  Flow rate: 0.6 ml/min
  Detection wavelength: 254 nm
  Retention time: 19.1 minutes
Amino acid analysis in the acid decomposition products (decomposition products after treating with 6 N hydrochloric acid-phenol at 110° C. for 24 hours)
  Asx 46.9 (50), Glx 49.9 (52), Ser 39.8 (48), Gly 44.1 (43), His 14.1 (16), Arg 32.2 (35), Thr 21.5 (25), Ala* 32 (32), Pro 26.6 (29), Tyr 21.5 (24), Val 21.8 (25), Met 2.9 (5), Ile 17.1 (19), Leu 37.0 (39), Phe 14.9 (19), Lys 18.0 (16), Cys—(35), Trp—(13)
* standard amino acid; data within parentheses indicate calculated data; symbol—indicates data not measured.

Physical Property of Product B

High performance gel filtration chromatography
  Column: TSK-gel G3000PW 7.5 mm$\phi$×600 nun (manufactured by TOSO Co., Ltd.)
  Eluant: 0.2M aqueous sodium chloride solution
  Flow rate: 0.6 ml/min
  Detection wavelength: 254 nm
  Retention time: 20.6 minutes
Amino acid analysis in the acid decomposition products (decomposition products after treating with 6 N hydrochloric acid-phenol at 110° C. for 24 hours)
  Asx 48.3 (50), Glx 52.7 (52), Ser 46.5 (48), Gly 46.5 (43), His 14.8 (16), Arg 33.5 (35), Thr 20.2 (25), Ala* 32 (32), Pro 29.0 (29), Tyr 23.5 (24), Val 22.8 (25), Met 2.9 (5), Ile 17.2 (19), Leu 39.8 (39), Phe 16.0 (19), Lys 20.4 (16), Cys—(35), Trp—(13)
* standard amino acid; data within parentheses indicate calculated data; symbol—indicates data not measured.

EXAMPLE 66

PEG2-modified human endothelin

In 150 μl of 0.1M borate buffer (pH 10) was dissolved 250 μg of human endothelin and, 6 mg of high purity PEG2 prepared in Example 1 was added to the solution at 4° C. The mixture was allowed to stand at 4° C. for 5 hours. After neutralizing with 1N acetic acid, purification was performed by gel filtration using TSK G3000SW [7.5 mm$\phi$×600 mm, 0.1M aqueous sodium chloride solution (containing 5% ethanol)]. The fraction containing the desired product was desalted and concentrated to give 60 μl of an aqueous solution containing the product.

Physical Property

High performance gel filtration chromatography
  Column: TSK-gel G3000SW 7.5 mm$\phi$×600 mm (manufactured by TOSO Co., Ltd.)
  Eluant: 0.1M aqueous sodium chloride solution (containing 5% ethanol)
  Flow rate: 0.7 ml/min
  Detection wavelength: 220 nm
  Retention time: 19.1 minutes
Amino acid analysis in the acid decomposition products (decomposition products after treating with 6 N hydrochloric acid-phenol at 110° C. for 24 hours)
  Asx 1.9 (2), Glx 1.0 (1), Set 2.8 (3), His 0.9 (1), Tyr 1.0 (1), Val 1.0 (1), Met 0.4 (1), Ile 1.2 (2), Leu 2.2 (2), Phe* 1 (1), Lys 0.9 (1), Cys—(4), Trp—(1)
* standard amino acid; data within parentheses indicate calculated ones; symbol—indicates data not measured.

EXAMPLE 67

PEG2-modified oxytocin

In 40 μl of water was dissolved 0.46 mg of oxytocin and, 210 μl of 0.1M borate buffer (pH 10) was added to the solution. Thereafter, 22.6 mg of high purity PEG2 prepared in Example 1 was added to the mixture. The resulting mixture was allowed to stand at 4° C. for 17.5 hours. After 200 μl of water was added thereto, the mixture was neutralized with 9N acetic acid. Then, purification was performed by reverse phase high performance liquid chromatography [YMC-ODS, 4.6 mm$\phi$×250 mm; gradient using eluant A=water-containing 0.1% TFA and eluant B=acetonitrile (0.1% TFA) (initial concentration of eluant B: 25%, gradient: 1%/min); flow rate: 1 ml/min]. After the fraction containing the product was freeze dried, 100 μl of water was added to give an aqueous solution containing the desired product.

Physical Property

Reverse phase high performance liquid chromatography
  Column: YMC-ODS AM303, 4.6 mm$\phi$×250 mm (manufactured by Yamamura Chemical Co., Ltd.)
  Eluant: gradient
    eluant A: water (0.1% trifluoroacetic acid)
    eluant B: acetonitrile (0.1% trifluoroacetic acid)
  initial concentration of eluant B: 25%
  concentration gradient: 1%/min
  Flow rate: 1 ml/min
  Detection wavelength: 220 nm
  Retention time: 27.5 minutes Amino acid analysis in the acid decomposition products (decomposition products after treating with 6 N hydrochloric acid-phenol at 110° C. for 24 hours)
Asx 1.0 (1), Glx 1.0 (1), Gly 1.1 (1), Pro 1.0 (1), Tyr 1.0 (1), Cys—(2), Ile 1.0 (1), Leu* 1 (1)

* standard amino acid; data within parentheses indicate calculated ones; symbol—indicates data not measured.

EXAMPLE 68

PEG2-modified [His$^1$, Lys6]-GHRP
(H-His-D-Trp-Ala-Trp-D-Phe-Lys-NH$_2$)

In 1 ml of 0.1M borate buffer (pH 10) was dissolved 3 mg of [Hisl, Lys$^6$]-GHRP and, 206 mg of high purity PEG2 prepared in Example 1 was added to the solution. The resulting mixture was allowed to stand at 4° C. for 6.5 hours. After 500 μl of 0.1M borate buffer (pH 10) and 50 mg of PEG2 were added thereto, 500 μl of acetonitrile, 500 pl of 0.1M borate buffer (pH 10) and 50 mg of PEG2 were further added thereto 20.5 hours after and 500 pl of 0.1M borate buffer (pH 10) and 50 mg of PEG2 were further added 24 hours after. Then 50 mg of PEG2 was added further 24 hours after. The mixture was allowed to stand at 4° C. for 21 hours. After 3 ml of water was added to the mixture, it was neutralized with 9N acetic acid. Then, purification was performed by reverse phase high performance liquid chromatography [YMC-ODS, 10 mmφ×250 mm; gradient using eluant A=water-containing 0.1% TFA and eluant B=acetonitrile (0.1% TFA) (initial concentration of eluant B: 25%, gradient: 1%/min); flow rate: 3 ml/min]. After the fraction containing the product was freeze dried, 500 μl of water was added to give an aqueous solution containing the desired product.

Physical Property

Reverse phase high performance liquid chromatography
  Column: YMC-ODS AM303, 4.6 mmφ×250 mm (manufactured by Yamamura Chemical Co., Ltd.)
  Eluant: gradient
    eluant A: water (0.1% trifluoroacetic acid)
    eluant B: acetonitrile (0.1% trifluoroacetic acid)
  initial concentration of eluant B: 25%
  concentration gradient: 1%/min
  Flow rate: 1 ml/min
  Detection wavelength: 220 nm
  Retention time: 28.6 minutes
Amino acid analysis in the acid decomposition products (decomposition products after treating with 6 N hydrochloric acid-phenol at 110° C. for 24 hours)
  His 0.9 (1), Ala* 1 (1), Phe 1.0 (1), Lys 1.0 (1), Trp—(2)

* standard amino acid; data within parentheses indicate calculated ones; symbol—indicates data not measured.

EXAMPLE 69

PEG2-modified [D-Arg$^1$, D-Pro$^2$, D-Trp$^{7,9}$, Leu11]-substance P

In 500 μl of 0.1M borate buffer (pH 10) was dissolved 1 mg of [D-Arg$^1$, D-Pro$^2$, D-Trp$^{7,9}$, Leu$^{11}$]-substance P and, 40.1 mg of high purity PEG2 prepared in Example 1 was added to the solution. The resulting mixture was allowed to stand at 4° C. for 30 hours. After 500 μl of water was added thereto, the mixture was neutralized with 9N acetic acid. Then, purification was performed by reverse phase high performance liquid chromatography [YMC-ODS, 10 mmφ×250 mm; gradient using eluant A=water-containing 0.1% TFA and eluant B=acetonitrile (0.1% TFA) (initial concentration of eluant B: 25%, gradient: 1%/min); flow rate: 3 ml/min]. The fractions containing Product A and Product B were collected, respectively. After freeze drying, respectively, 100 μl each of water was added thereto to give aqueous solutions containing Product A and Product B, respectively.

Physical Property of Product A

Reverse phase high performance liquid chromatography
  Column: YMC-ODS AM303, 4.6 mmφ×250 nun (manufactured by Yamamura Chemical Co., Ltd.)
  Eluant: gradient
    eluant A: water (0.1% trifluoroacetic acid)
    eluant B: acetonitrile (0.1% trifluoroacetic acid)
  initial concentration of eluant B: 25%
  concentration gradient: 1%/min
  Flow rate: 1 ml/min
  Detection wavelength: 220 nm
  Retention time: 31.2 minutes
Amino acid analysis in the acid decomposition products (decomposition products after treating with 6 N hydrochloric acid-phenol at 110° C. for 24 hours)
  Glx 1.9 (2), Arg 1.0 (1), Pro 2.3 (2), Leu* 2 (2), Phe 1.0 (1), Lys 0.8 (1), Trp—(2)

* standard amino acid; data within parentheses indicate calculated data; symbol—indicates data not measured.

Physical Property of Product B

Reverse phase high performance liquid chromatography
  Column: YMC-ODS AM303, 4.6 mmφ×250 mm (manufactured by Yamamura Chemical Co., Ltd.)
  Eluant: gradient
    eluant A: water (0.1% trifluoroacetic acid)
    eluant B: acetonitrile (0.1% trifluoroacetic acid)
  initial concentration of eluant B: 25%
  concentration gradient: 1%/min
  Flow rate: 1 ml/min
  Detection wavelength: 220 nm
  Retention time: 31.5 minutes
Amino acid analysis in the acid decomposition products (decomposition products after treating with 6 N hydrochloric acid-phenol at 110° C. for 24 hours)
  Glx 1.6 (2), Arg 1.1 (1), Pro 2.3 (2), Leu* 2 (2), Phe 0.9 (1), Lys 0.9 (1), Trp—(2)

* standard amino acid; data within parentheses indicate calculated data; symbol—indicates data not measured.

EXAMPLE 70

PEG2-modified asparaginase

After 975 mg of asparaginase was dissolved in 195 ml of 0.1M borate buffer (pH 10.0), 29.0 g of high purity PEG2 prepared in Example 1 was added to the solution at 4° C. over 60 minutes by dividing PEG2 into 3 portions. After stirring at 4° C. for further 22 hours, water was added to the mixture to make the volume 4.5 liters. After neutralizing with 5% aqueous acetic acid solution, 6.5 l of the desired product was obtained by ultrafiltration as an aqueous solution of protein content of 0.14 mg/ml.

Physical Property

High performance gel filtration chromatography
  Column: TSK-gel G4000$_{PWXL}$ [(7.8 mmφ×30 cm)×2, guard column, TSK guard column PW$_{XL}$ (6.0 mmφ×4 cm (manufactured by TOSO Co., Ltd.)]

Eluant: 0.2M aqueous sodium chloride solution
Flow rate: 0.6 ml/min
Detection wavelength: 254 nm
Retention time: 24.3 minutes

EXAMPLE 71

PEG2-modified human erythrocyte derived Cu, Zn-SOD

After 40 ml of 0.1M borate buffer (pH 10.0) was added to 100 mg of human erythrocyte-derived Cu, Zn-SOD, the mixture was cooled to 5° C. and 7.0 g of high purity PEG2 prepared in Example 1 was added to the mixture at 5° C. After vigorously stirring, the resulting mixture was allowed to stand at 5° C. for 9 hours. After completion of the reaction, pH of the mixture was adjusted to 6.2 with 2N aqueous acetic acid solution. The reaction mixture was purified by ultrafiltration [using YM-30 membrane, manufactured by Amicon Co., Ltd.]. The resulting aqueous solution (40 ml) was divided into 4 aliquats, which were applied to Sephacryl S-200 column (2.6 cm$\phi$×81 cm; 0.2M aqueous sodium chloride solution) to purify by gel filtration. The fraction containing the product was collected. After desalting and concentrating by ultrafiltration using YM-30 membrane, manufactured by Amicon Co., Ltd.], 25 ml of an aqueous solution containing the desired product was obtained. The thus obtained modified product had an enzyme activity of 61% based on the unmodified SOD [cytochrome C method].

Physical Property

High performance gel filtration chromatography
Column: TSK-gel G3000PW 7.5 mm$\phi$×600 nun (manufactured by TOSO Co., Ltd.)
Eluant: 0.2M aqueous sodium chloride solution
Flow rate: 0.6 ml/min
Detection wavelength: 220 nm
Retention time: 18.55 minutes
Amino acid analysis in the acid decomposition products (decomposition products after treating with 6 N hydrochloric acid-phenol at 110° C. for 24 hours)
Asx 33.0 (36), Glx 24.3 (26), Ser 17.4 (20), Gly 45.2 (50), His 13.8 (16), Arg 6.53 (8), Thr 14.7 (16), Ala* 20.0 (20), Pro 10.7 (10), Val 21.2 (28), Ile 10.5 (18), Leu 15.7 (18), Phe 6.99 (8), Lys 14.2 (22)
* standard amino acid; data within parentheses indicate calculated data; symbol—indicates data not measured.
Degree of modification; 65% (TNBS method)

EXAMPLE 72

PEG2-modyfied human urine erythropoietin

To 50 $\mu$l of 0.05M borate buffer (pH9.5) containing 0.1 mg erythropoietin was added 2 mg of high purity PEG2 prepared in Example 1 at 4° C. and the resulting mixture was allowed to stand at 4° C. Further 2 hours after, 1 mg of PEG2 was added to the mixture, which was allowed to stand at 4° C. for 18 hours. After neutralizing with 0.1M acetic acid, the mixture was then desalted and concentrated by ultrafiltration. The concentrate was purified through gel filtration by passing through Sephacryl S-200 column (2.6 cm$\phi$×94cm: 0.2M aqueous sodium chloride solution). The fraction containing the product was collected. After desalting and concentrating by ultrafiltration, 1.0 ml of an aqueous solution containing the desired product was obtained. The thus obtained modified product had activity of 65% on the unmodified erythropoietin (in vitro assay of erythropoietin in fetal mouse liver culture, British Journal of Haematology, 1981, 47, 461–468).

Physical Property

Reverse phase high performance liquid chromatography
column: YMC-ODS AM303, 4.6 mm$\phi$×250 mm (manufactured by Yamamura Chemical Co., Ltd.)
Eluant: gradient
  eluant A: water (0.1% trifluoroacetic acid)
  eluant B: acetonitrile (0.1% trifluoroacetic acid)
initial concentration of eluant B: 30%
concentration gradient: 1%/min
flow rate: 1ml/min
detection wavelength: 214nm
retention time: 15.02 minutes

What is claimed is:

1. A process for preparing a polyethylene glycol derivative represented by formula (I):

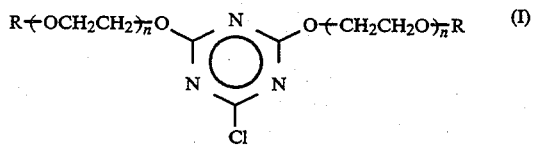

wherein R represents an alkyl group and n represents an optionally variable positive integer, which comprises reacting a polyethylene glycol mono-alkyl ether compound represented by the formula (II):

$$R-(OCH_2CH_2)_n-OH \qquad (II)$$

wherein R and n have the same significances as described above, with cyanuric chloride in the presence of an oxide of a metal belonging to Group IIB.

2. A process according to claim 1, wherein said metal oxide is selected from the group consisting of zinc oxide, cadmium oxide and mercury oxide.

* * * * *